(12) United States Patent
Hedman et al.

(10) Patent No.: US 8,198,248 B2
(45) Date of Patent: *Jun. 12, 2012

(54) FORMULATIONS FOR NONSURGICAL EXOGENOUS CROSSLINK THERAPY

(75) Inventors: Thomas P. Hedman, Georgetown, TX (US); Paul Slusarewicz, Austin, TX (US)

(73) Assignee: Orthopeutics, LP, Lexington, KY (US)

( * ) Notice: Subject to any disclaimer, the term of this patent is extended or adjusted under 35 U.S.C. 154(b) by 781 days.

This patent is subject to a terminal disclaimer.

(21) Appl. No.: 12/203,730

(22) Filed: Sep. 3, 2008

(65) Prior Publication Data

US 2010/0041616 A1   Feb. 18, 2010

Related U.S. Application Data

(63) Continuation-in-part of application No. 12/192,746, filed on Aug. 15, 2008.

(51) Int. Cl.
*A61K 31/352* (2006.01)
(52) U.S. Cl. .......................................... 514/23; 514/456
(58) Field of Classification Search .................... 514/23, 514/456
See application file for complete search history.

(56) References Cited

U.S. PATENT DOCUMENTS

| | | | |
|---|---|---|---|
| 6,375,672 B1* | 4/2002 | Aksan et al. ..................... | 607/96 |
| 6,812,211 B2 | 11/2004 | Slivka et al. ..................... | 514/12 |
| 7,208,171 B2 | 4/2007 | Messersmith et al. | |
| 7,435,722 B2 | 10/2008 | Hedman ........................ | 514/23 |
| 2006/0134170 A1 | 6/2006 | Griffith et al. | |
| 2007/0183973 A1 | 8/2007 | Hedman ...................... | 424/1.73 |
| 2007/0196351 A1 | 8/2007 | Hedman ...................... | 424/94.4 |
| 2007/0202143 A1 | 8/2007 | Hedman ...................... | 424/422 |
| 2007/0248567 A1 | 10/2007 | Pathak et al. .............. | 424/78.27 |
| 2008/0064021 A1 | 3/2008 | Hedman et al. ............... | 435/1.1 |
| 2008/0260712 A1 | 10/2008 | Hedman ...................... | 424/94.4 |

OTHER PUBLICATIONS

Kleunen, J. P. V., Summer Bioengineering Conference, Jun. 25-29, 2003, pp. 1-2.*
Hedman et al, Spine, 2006, 31(15), E480-E485.*
Lee et al, J. Biomed. Material Res., 1989, 23, 457-75.*
International Search Report and Written Opinion, issued in PCT/US2010/040610, mailed Sep. 1, 2010.
Boyd-White and Williams, "Effect of cross-linking on matrix permeability. A model for AGE-modified basement membranes," *Diabetes*, 45:348-353, 1996.
Buckwalter, "Aging and degeneration of the human intervertebral disc," *Spine*, 20:1307-14, 1995.
Chachra et al., "Effect of applied uniaxial stress on rate and mechanical effects of cross-linking in tissue-derived biomaterials," *Biomaterials*, 17;1865-75, 1996.
Chellan and Nagaraj, "Protein crosslinking by the Maillard reaction: dicarbonyl-derived imidazolium crosslinks in aging and diabetes," *Arch. Biochem. Biophys.*, 368:98-104, 1999.
Chung et al., "Mechanism of action of guinea pig liver transglutaminase. VII. Chemical and stereochemical aspects of substrate binding and catalysis," *J. Biol. Chem.*, 245:6424-6435, 1970.
Duance et al., "Changes in collagen cross-linking in degenerative disc disease and scoliosis," *Spine*, 23:2545-51, 1998.
Fu et al., "Role of oxygen in cross-linking and chemical modification of collagen by glucose," *Diabetes*, 41 Suppl. 2:42-48, 1992.
Greve et al., "Collagen crosslinking and cartilage glycosaminoglycan composition in normal and scoliotic chickens," *Biochemica et Biophysica Acta*, 967:275-283, 1988.
Hedman et al., "Strength reduction of the posterior intervertebral disc resulting from repetitive sub-failure loading," *Orthop. Res. Soc. Transactions*, 24:1017, 1999.
Hedman and Gray, "Quantification of intervertebral disc degradation resulting from fatigue," *Orthop. Res. Soc. Transactions*, 27:120, 2002.
Horner et al., "2001 Volvo Award Winner in Basic Science Studies: Effect of nutrient supply on the viability of cells from the nucleus pulposus of the intervertebral disc," *Spine*, 26:2543-9, 2001.
Kitano et al., "Biochemical changes associated with the symptomatic human intervertebral disk," *Clinical Orthopedics and Related Res.*, 372-7, 1993.
Lee et al., "The bovine pericardial xenograft: I. Effect of fixation in aldehydes without constraint on the tensile viscoelastic properties of bovine pericardium,"*Journal of Biomedical Materials Research*, 23:457-475, 1989.
Murata-Kamiya and Kamiya, "Methylglyoxal, an endogenous aldehyde, crosslinks DNA polymerase and the substrate DNA," *Nucleic Acids Res.*, 29:3433-3438, 2001.
Sung et al., "Mechanical properties of a porcine aortic valve fixed with a naturally occurring crosslinking agent," *Biomaterials*, 20:1759-1772, 1999.
Sung et al.,"Crosslinking characteristics and mechanical properties of a bovine pericardium fixed with a naturally occurring crosslinking agent," *J.Biomed Materials Res.*, 47:116-126, 1999.
Sung et al., "Crosslinking of biological tissues using genipin and/or carbodiimide," *J. Biomed. Materials Res.*, 64:427-438, 2003.
Thompson et al., "Bone indentation recovery time correlates with bond reforming time," *Nature*, 414:773-776, 2001.
Wang et al., "Changes in the fracture toughness of bone may not be reflected in its mineral density, porosity, and tensile properties," *Bone*, 23:67-72, 1998.
Watkins et al., "Effect of phosphate on the kinetics and specificity of glycation of protein," *J. Biol. Chem.*, 262:7207-7212, 1987.
Zeeman et al., "Crosslinking and modification of dermal sheep collagen using 1, 4-butanediol diglycidyl ether," *J. Biomed. Materials Res.*, 46:424-433, 1999.
Zhang and Vogel, "Determination of the side chain pKa values of the lysine residues in calmodulin," *J. Biol. Chem.*, 268:22420-22428, 1993.
Zhang et al., "Cross-linking phosphatidylinositol-specific phospholipase C traps two activating phosphatidylcholine molecules on the enzyme," *J. Biol. Chem.*, 279:20490-20500, 2004.
Dec. 6, 2011 Office Action issued in U.S. Appl. No. 12/496,045.
Amresco literature, "Buffers: Quality, Consistency, Reliability", published 2001 by Amresco®, pp. 1-10.

* cited by examiner

*Primary Examiner* — Shaojia Anna Jiang
*Assistant Examiner* — Ganapathy Krishnan
(74) *Attorney, Agent, or Firm* — Berliner & Associates

(57) ABSTRACT

Improved methods and compositions for the treatment of native tissues with crosslinkers are provided. The methods and compositions will find particular use in increasing resistance to tearing, fissuring, rupturing, and/or delamination.

5 Claims, 16 Drawing Sheets

FIG. 11A-B

FORMULATIONS FOR NONSURGICAL EXOGENOUS CROSSLINK THERAPY

CROSS-REFERENCE TO RELATED APPLICATIONS

This application is a continuation-in-part of co-pending U.S. patent application Ser. No. 12/192,746 filed Aug. 15, 2008, which is incorporated herein by reference in its entirety.

BACKGROUND OF THE INVENTION

1. Field of the Invention

The present invention relates to a method for treatment of tissue, for example, collagenous tissue, where a deleterious mechanical loading environment contributes to the degradation of the tissue.

2. Description of the Related Art

Deleterious mechanical loading environments contribute to the degradation of collagenous tissue in a variety of manners. For instance, fatigue is a weakening of a material due to repetitive applied stress. Fatigue failure is simply a failure where repetitive stresses have weakened a material such that it fails below the original ultimate stress level. Elevated stress levels, due to tissue removal, can accelerate fatigue degradation of the remaining joint tissues. In bone and other diarthrodial joint tissues, two processes—biological repair and fatigue—are in opposition, and repair generally dominates. In the intervertebral disc, the prevalence of mechanical degradation of the posterior annulus (Osti, 1992) suggests that fatigue is the dominant process. The intervertebral disc, being the largest, principally avascular load supporting tissue in the body, is somewhat unique in this predisposition toward ongoing fatigue degradation. Another example would be the knee meniscus. Active tissue response (adaptation, repair) does not play a strong role in the case of mature intervertebral disc annular material. The intervertebral disc is comprised of three parts: the nucleus pulposus (NP) or nucleus, the annulus fibrosus (AF) or annulus, and the cartilaginous endplates. The characteristics of the inner annulus and outer nucleus blend with ongoing degeneration, with the nucleus becoming more fibrous and decreasing in water content. Similarly, the boundary between outer nucleus and inner annulus is known to fade and becomes indistinct with ongoing degeneration. As a principally avascular structure, the disc relies on diffusion and loading induced convection for nutrition of its limited number of viable cells. Age related changes interfere with diffusion presumably contributing to declining cell viability and biosynthetic function (Buckwalter et al., 1993; Buckwalter, 1995). Age related decline in numbers of cells and cell functionality compromises the ability of the cells to repair mechanical damage to the matrix. Some regeneration of the matrix in the nucleus following enzymatic degradation has been accomplished, albeit inconsistently (Deutman, 1992). Regeneration of functional annular material has not yet been realized.

Combined with this limited potential for repair or regeneration, studies have shown that posterior intervertebral disc tissue is vulnerable to degradation and fatigue failure when subjected to non-traumatic, physiologic cyclic loads. Prior work has shown deterioration in elastic-plastic (Hedman, 1999) and viscoelastic (Hedman, 2000) material properties in posterior intervertebral disc tissue subjected to moderate physiological cyclic loading. Cyclic load magnitudes of 30% of ultimate tensile strength produced significant deterioration of material properties with as little as 2000 cycles. Green (1993) investigated the ultimate tensile strength and fatigue life of matched pairs of outer annulus specimens. They found that fatigue failure could occur in less than 10,000 cycles when the vertical tensile cyclic peak exceeded 45% of the ultimate tensile stress of the matched pair control. In addition, Panjabi et al. (1996) found that single cycle sub-failure strains to anterior cruciate ligaments of the knee alter the elastic characteristics (load-deformation) of the ligament. Osti (1992) found that annular tears and fissures were predominantly found in the posterolateral regions of the discs. Adams (1982) demonstrated the propensity of slightly degenerated discs to prolapse posteriorly when hyperflexed and showed that fatigue failure might occur in lumbar discs as the outer posterior annulus is overstretched in the vertical direction while severely loaded in flexion. In an analytical study, interlaminar shear stresses, which can produce delaminations, have been found to be highest in the posterolateral regions of the disc (Goel, 1995). These data indicate: 1) posterior disc and posterior longitudinal ligament are at risk of degenerative changes, and 2) the mechanism of degeneration can involve flexion fatigue.

A different type of mechanical degradation of collagenous tissue occurs in scoliosis and other progressive spinal deformities. Scoliosis refers to an abnormal lateral, primarily, or other curvature or deformity of the spine, often of unknown origin. Degenerative scoliosis refers to the often painful progression of deformity resulting from degeneration of discs and other spinal tissues. Progressive spinal deformities can also occur subsequent to surgical bone removal, with or without accompanying spinal instrumentation, such as in a neural decompression procedure or subsequent to vertebral failure. The bony vertebral failure itself may occur as a result of trauma or of age related osteoporosis or osteopenia. Kyphotic deformity (loss of outward concavity or increase in outward convexity), in the lumbar spine also known as flat-back syndrome, is a frequent sequela to spinal fusion or installation of spinal instrumentation, especially in the case of a long, multi-level, surgical construct. Severe curvature and ongoing curve progression can lead to many other health disorders including but not limited to compromised respiratory function. In addition, one's lifestyle can be adversely affected and a loss of cosmesis can result. A large segment of the population is affected by scoliosis, approximately 2% of women and 0.5% of men. Over 80% of scoliosis is of no known origin (i.e., idiopathic). Approximately 80% of idiopathic scoliosis develops in young pubescent adults. The incidence of deformity increases with age. Existing conservative approaches to limit curve progression such as external bracing can be awkward or restricting, are associated with high patient non-compliance, and are of disputed value. Surgical correction of severe curves can be intensive with a long recovery period, require post-operative bracing, and be fraught with many other post-operative problems.

Another form of spinal deformity, spondylolisthesis commonly occurs in the lower lumbar region of the spine. Spondylolisthesis involves the slippage of one vertebral level relative to an adjacent level. Progressive listhesis leads to sciatica and pain. Surgical intervention is an option to prevent progressive slip, especially when the slip has reached a greater amount of slip displacement or slip angle. However, nonsurgical means of preventing a slip to progress to the point where surgery is indicated have not been available previously.

Current treatments for scoliosis and other progressive spinal deformities consist of bracing and surgery. The purpose of orthopaedic braces is to prevent increasing spinal deformity, not to correct existing deformity. Braces are generally used in children with an expected amount of skeletal growth remaining, who have curve magnitudes in the range of 25 to 40 degrees. External braces are routinely used as a standard of care. Yet there is controversy regarding the effectiveness of external bracing. The magnitude of forces delivered to the spine corresponding to brace loads applied to the torso cannot be quantified directly. Larger forces applied to the torso may also result in brace induced pathologies to the tissues in contact with the brace. Some studies suggest that braces are effective in halting curve progression in about 80% of afflicted children. But because the option to do nothing but observe curve progression is inappropriate, there is no generally accepted percentage of these curves that would stop progressing on their own or due to other factors. Clearly, improved methods of treating such disorders is urgently required.

SUMMARY OF THE INVENTION

Thus, in accordance with the present invention, there is provided a method of inducing methylglyoxal (MG)-mediated cross-linking in a native tissue having naturally-occurring collagen crosslinks within a living human body comprising contacting said tissue with MG at 5-50 mM and any combination of the following in a composition of about pH 8.0-9.5: (a) 4-(2-Hydroxyethyl)-1-piperazinepropanesulfonic acid (EPPS) buffer at 50-250 mM; (b) 50-500 mM phosphate ions; (c) sodium borohydride at about 1-5 mM; and/or (d) a surfactant. For example, MG may be contacted in at a concentration of 20 mM in 100 mM 4-(2-Hydroxyethyl)-1-piperazinepropanesulfonic acid (EPPS) buffer at pH 9 with 100 mM phosphate ions. The tissue may be located in a joint; the tissue is a spinal disc.

In another embodiment, there is provided a method of inducing genipin (GP)-mediated cross-linking in a native tissue having naturally-occurring collagen crosslinks within a living human body comprising contacting said tissue with GP at about 20 mM or less and any combination of the following in a composition of about pH 8.0-9.5: (a) 50-500 mM phosphate ions; (b) 50-250 mM EPPS buffer; and/or (c) a surfactant. For example, GP may be contacted at a concentration of 10 mM in 100 mM EPPS buffer at pH 9 with 100 mM phosphate ions. The tissue may be located in a joint; the tissue is a spinal disc.

In yet another embodiment, there is provided a method of inducing proanthrocyanidin (PA)-mediated cross-linking in a native tissue having naturally-occurring collagen crosslinks within a living human body comprising contacting said tissue with about 0.025-0.5% w/v PA and any combination of the following in a composition of about pH 5-9.5: (a) 50-25 mM Tris buffer; and/or (b) a surfactant. For example, PA may be contacted at about 0.1% w/v of said composition containing 100 mM Tris buffer at pH 9. The tissue may be located in a joint; the tissue is a spinal disc.

In still yet another embodiment, there is provided a method of inducing transglutaminase (TG)-mediated cross-linking in a native tissue having naturally-occurring collagen crosslinks within a living human body comprising contacting said tissue with a composition comprising about 0.5-5 U/ml TG and any combination of the following at about pH 7-8: (a) 50-250 mM tris buffer; and/or (b) a surfactant. For example, TG may be contacted at 2 U/ml in 100 mM Tris buffer at pH 8. The tissue may be located in a joint; the tissue is a spinal disc.

In a further embodiment, there is provided a method of inducing 1-Ethyl-3-[3-dimethylaminopropyl]carbodiimide (EDC)-mediated cross-linking in a native tissue having naturally-occurring collagen cross-links within a living human body comprising contacting said tissue with about 2-10 mM EDC and any combination of the following in a composition of about pH 6.0: (a) 50-150 mM; and/or (b) a surfactant. For example, EDC may be contacted at a concentration of 5 mM in a buffer lacking amine or carboxyl groups. The buffer may be 100 mM 2-(N-morpholino)ethanesulfonic acid (MES). The tissue may be located in a joint; the tissue is a spinal disc.

In yet a further embodiment, there is provided a method of inducing L- or D-threose (LT or DT)-mediated cross-linking in a native tissue having naturally-occurring collagen crosslinks within a living human body comprising contacting said tissue with 20-100 mM LT or DT and any combination of the following in a composition of about pH 7-9: (a) 50-250 mM EPPS buffer; (b) 50-250 mM phosphate ions; (c) sodium borohydride at about 1-5 mM; and/or (d) a surfactant. For example, LT or DT may be contacted at about 100 mM in EPPS buffer at pH 9 with 100 mM phosphate ions. The tissue may be located in a joint; the tissue is a spinal disc.

In still yet a further embodiment, there is provided a method of inducing cross-linking in a native tissue having naturally-occurring collagen crosslinks within a living human body comprising contacting said tissue with a cross-linking agent and an anionic surfactant. The cross-linking agent may be genipin, methylglyoxal, proanthrocyanidin, L-threose, D-threose, ribose, glyoxal, lysyl oxidase, an epoxy, 1-Ethyl-3-[3-dimethylaminopropyl]carbodiimide or transglutaminase. The anionic surfactant may be an alkyl sulfonate, sodium cholate, sodium deoxycholate, an alkyl benzene sulfonate, N-lauroylsarcosine, or a fatty acid salt. The tissue may be located in a joint; the tissue is a spinal disc.

Also provided are:
  a composition of matter comprising about 5-50 mM methylglyoxal (MG) and about 50-250 mM EPPS at about pH 8.0-9.5 and 50-500 mM phosphate ions;
  a composition of matter comprising about 5-20 mM genipin (GP) and about 50-250 mM EPPS at about pH 8.0-9.5 and 50-500 mM phosphate ions;
  a composition of matter comprising about 0.025-0.5% w/v of proanthrocyanidin (PA) and about 50-250 mM Tris at about pH 8.0-9.5;
  a composition of matter comprising about 20-100 mM L- or D-threose (LT or DT) and about 50-250 mM EPPS at about pH 8.0-9.5 and phosphate ions at about 50-500 mM;

An additional embodiment, there is provided a method of inducing cross-linking in a native tissue having naturally-occurring collagen crosslinks within a living human body comprising contacting said tissue with any combination of methylglyoxal at 5-50 mM, genipin at about 20 mM or less, about 0.025-0.5% w/v proanthrocyanidin, about 0.5-5 U/ml transglutaminase, 2-10 mM 1-Ethyl-3-[3-dimethylaminopropyl]carbodiimide (EDC), 20-100 mM L- or D-threose. The combination may genipin at about 20 mM or less and any of the foregoing other crosslinkers. Particular combinations include methylglyoxal at 5-50 mM and genipin at about 20 mM or less, 20-100 mM L- or D-threose and genipin at about 20 mM or less, about 0.025-0.5% w/v proanthrocyanidin and genipin at about 20 mM or less, and about 0.025-0.5% w/v about 0.5-5 U/ml transglutaminase and genipin at about 20 mM or less. In addition, any of the preceding combinations may also include phosphate ions, surfactants, and/or sodium borohydride.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions and kits of the invention can be used to achieve methods of the invention.

Throughout this application, the term "about" is used to indicate that a value includes the inherent variation of error for the device, the method being employed to determine the value, or the variation that exists among the study subjects.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
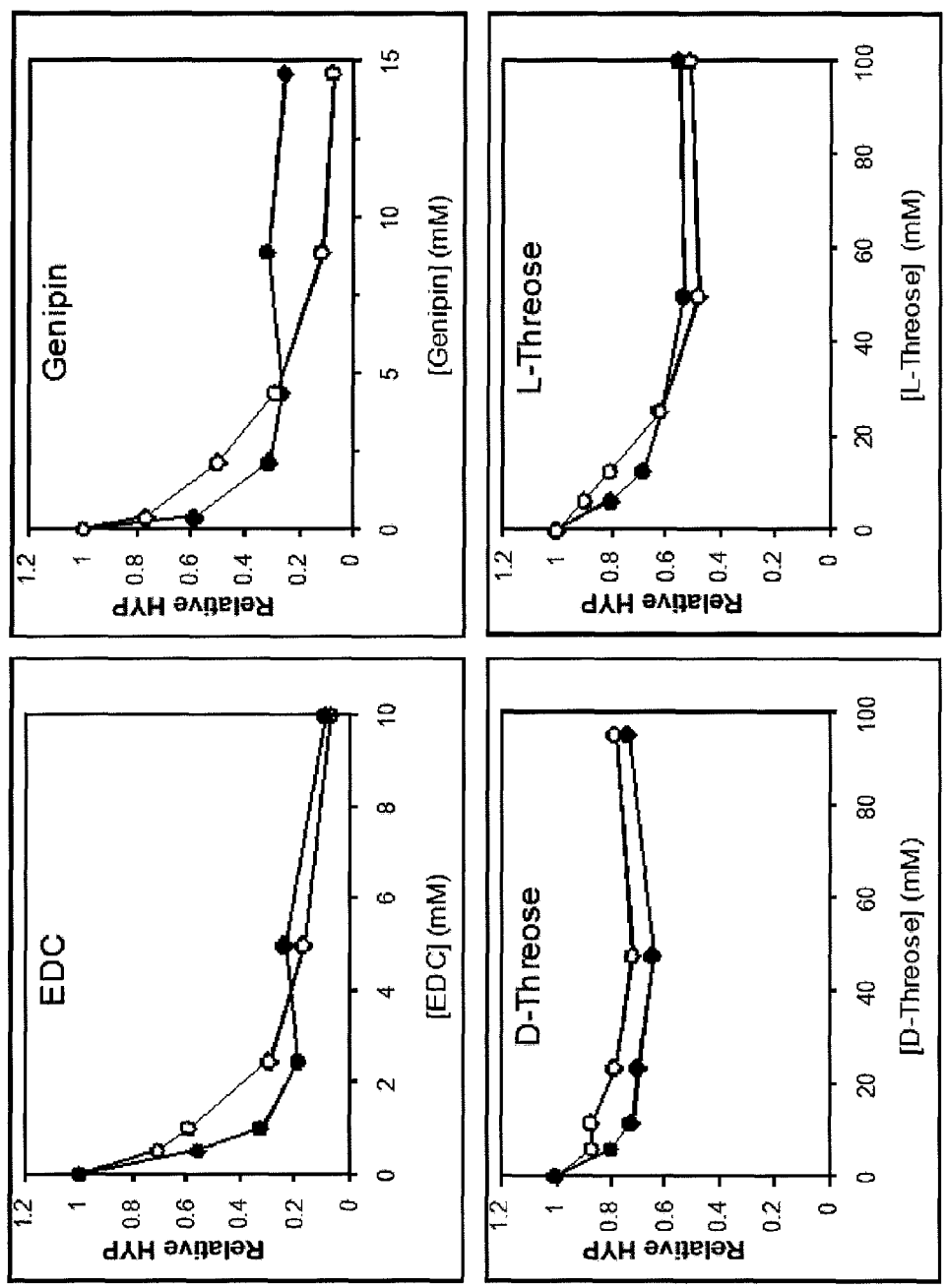
FIG. 1—Concentration dependence of protein crosslinking reagents. Increasing concentrations of protein crosslinkers were added to homogenized annulus tissue and incubated for either 1 hr (EDC, GP, MG, PA and GA), 2 hrs (TG) or 6 hrs (DT and LT). Crosslinking was quantified by determining the amount of hydroxyproline (HYP) released from the tissue by collagenase digestion.
Figure 1:
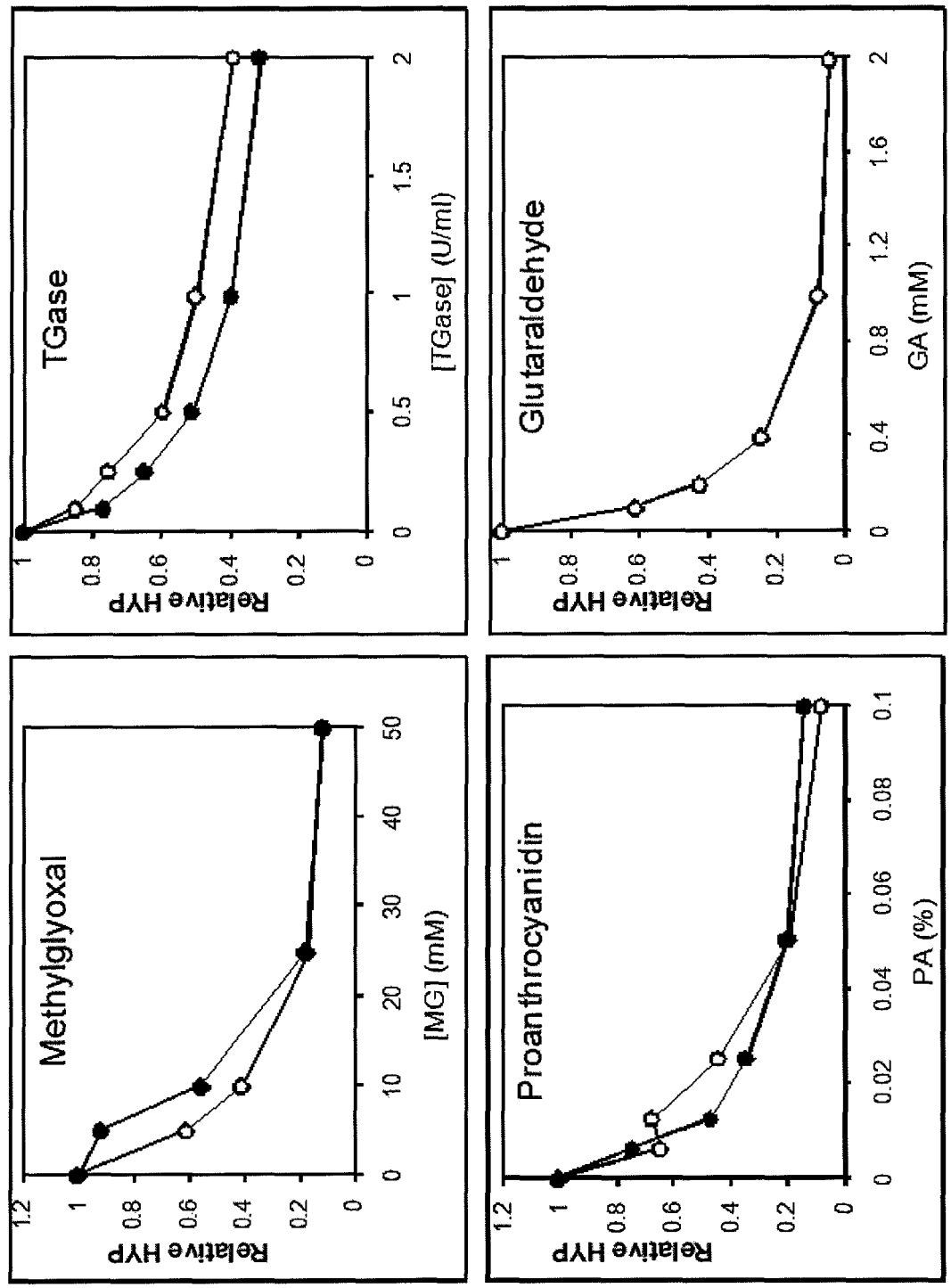

Stabilization of joints, in particular spinal discs, by treatment with exogenously administered cross-linking agents is a promising and novel approach to the treatment and/or prophylaxis of many common orthopedic indications such as degenerative disc disease (DDD), scoliosis and knee meniscus tears. Non-surgical exogenous cross-linking therapy (NEXT) would provide a paradigm shift in the treatment of such orthopedic conditions.

Crosslinking of the collagenous connective tissue of a joint is expected to stabilize the tissue, thus ameliorating the symptoms of the disease as well as slowing further progression. In the case of scoliosis it has been shown that natural, endogenous crosslinks accumulate at the side of the joint under the most tensile stress, presumably as a mechanism to counteract the gradual and growing curvature of the spine. In this case, exogenous crosslinking in these areas would help to support the body's own mechanism to counteract the growing curvature.

In order to increase the chance for success, the crosslinking agent needs to be carefully selected to confer the optimal biomechanical properties required to stabilize the joint in question in vitro and ex vivo. However, once such an agent has been selected, it is critical that it performs equally efficaciously in the in vivo context as it does in vitro. Thus, development of an optimal carrier vehicle that will ensure maximal crosslinking will occur in a clinically relevant period of time is critical in the development of such a technology.

The present invention therefore deals with improved compositions for treating joints to effect crosslinking in vivo. The inventors have identified pH ranges, unique combinations of crosslinking agents and buffers, crosslinking enhancers and surfactants, all of which improve the crosslinking of joint tissues.

I. Crosslinking of Tissues

Naturally occurring collagen crosslinks play an important role in stabilizing collagenous tissues and, in particular, the intervertebral disc. Significantly higher quantities of reducible (newly formed) crosslinks have been found on the convex sides than on the concave sides of scoliotic discs (Duance et al., 1998). Similarly, Greve et al. (1988) found a statistically significant increase in the amount of reducible crosslinks in scoliotic chicken discs preceding cessation of curve progression. Since reducible crosslinks represent an early stage in the formation of mature, non-reducible collagen crosslinks, this suggests that there is some form of natural, cell-mediated crosslink augmentation that occurs in response to the elevated tensile environment on the convex side of scoliotic discs. Greve et al. also found that there were fewer reducible crosslinks at the very early stages of development in the cartilage of scoliotic chickens. They concluded that differences in collagen crosslinking did not appear to be causative because there was not a smaller number of crosslinks at later stages of development. In fact, later on, when the scoliotic curve was progressing, there were statistically significant greater numbers of collagen crosslinks, perhaps in response to the curvature. Although not the conclusion of Greve et al., this can be interpreted as being a sufficient depletion of crosslinks in the developmental process with long enough duration to trigger the progression of scoliotic curvature that was later mended by a cellular response that produced higher than normal levels of crosslinks. These studies suggest that the presence of collagen crosslink augmentation mechanisms may be critical to prevent ongoing degradation and for mechanical stability of intervertebral disc tissue in scoliotic spines and when tensile stresses are elevated.

It is important to note that these studies did not quantify the integrity or crosslink quantities associated with the elastin and elastic fiber network which also plays a role in the mechanical integrity of these collagenous materials. Some of the benefit of crosslinking of the principally collagenous tissues like the intervertebral disc may also be attributed to an effect on the elastin and elastic fiber network and other proteins (such as link proteins) in these collagenous tissues. In the same way that intramolecular, intermolecular and interfibrillar crosslinks of collagen molecules and fibers benefit the tissue and joint mechanics, including resistance to degradation, tears and deformity, and increased permeability, intramolecular, intermolecular and interfibrillar crosslinks involving elastin and the elastic fiber network could provide benefits to the tissue and joint mechanics and nutrition. In fact, the same reagents effective at augmenting collagen crosslinking may also augment crosslinks involving the elastin and elastic fiber network, or other tissue proteins.

It is well documented that endogenous (naturally occurring—enzymatically derived and age increasing non-enzymatic) and exogenous collagen crosslinks (historically applied to implants) increase the strength and stiffness of collagenous, load-supporting tissues (Chachra, 1996; Wang, 1998; Sung, 1999a; Zeeman, 1999; Chen, 2001). Sung (1999b) found that a naturally occurring crosslinking agent, genipin, provided greater ultimate tensile strength and toughness when compared with other crosslinking reagents. Genipin also demonstrated significantly less cytotoxicity compared to other more commonly used crosslinking agents. With regard to viscoelastic properties, Lee (1989) found that aldehyde fixation reduced stress-relaxation and creep in bovine pericardium. Recently, naturally occurring collagen crosslinks were described as providing "sacrificial bonds" that both protect tissue and dissipate energy (Thompson et al., 2001). A need remains to find biochemical methods that enhance the body's own efforts to stabilize discs in scoliotic and other progressively deforming spines by increasing collagen crosslinks.

Mechanical degradation of collagenous tissue can also occur if the environment for biological activity in the central region of the disc is poor. Tissue engineering is a burgeoning field which aims to utilize cells, special proteins called cytokines and synthetic and native matrices or scaffolds in the repair and regeneration of degraded, injured or otherwise failed tissues. With regard to the intervertebral disc, biological solutions like tissue engineering are hindered by the harsh, hypoxic (oxygen-deficient) avascular (very little if any direct blood supply) environment of moderately degenerated intervertebral discs. The disc is known to receive nutrients and discard cell waste products primarily by diurnal-cyclic pressure driven fluid flow and diffusion through the annulus fibrosus and through the cartilaginous endplates that connect the disc to the bony, well vascularized, spinal vertebrae. The disc cartilaginous endplates lose permeability by calcification while the disc itself becomes clogged up with an accumulation of degraded matrix molecules and cell waste products. This loss of disc permeability effectively reduces the flow of nutrients to the cells and the flow of waste products from the cells in the interior central region of the disc, the nucleus pulposus. This loss of flow of nutrition to the disc causes a loss of cell functionality, cell senescence, and causes a fall in pH levels that further compromises cell function and may cause cell death (Buckwalter, 1995; Horner and Urban, 2001). Horner and Urban (2001) showed that density of viable cells was regulated by nutritional constraints such that a decline in glucose supply led to a decrease in viable cells. Boyd-White and Williams (1996) showed that crosslinking of basement membranes increased permeability of the membranes to macromolecules such as serum albumin, crosslinked albumin, and a series of fluorescein isothiocyanate dextrans of four different molecular sizes. It is herein suggested, then, that increased crosslinking of the annulus fibrosus and/or the endplates of intervertebral discs, though very different and more complex collagenous tissues than basement membranes, would provide for increased flow of glucose and other nutritional macromolecules to cells and waste products from the cells in the interior region of the disc, thus improving their viability.

Intervertebral disc herniation involves fissuring, rupture or tearing of the annulus fibrosus followed by displacement of the central portion of the disc posteriorly or posterolaterally through the torn tissue. The deformed or displaced disc protrusion can compress a nerve root and/or the spinal cord. Clinical symptoms associated with herniated disc include back pain and radiculopathy including leg pain, sciatica and muscle weakness. Treatments for herniated disc commonly comprise excision of the protruding disc segment and other tissues suspected to be involved with nerve compression and pain. Prior to tearing through the outer annular fibers the disc can bulge posteriorly potentially applying pressure to neural elements. Approximately a decade typically separates the first, acute incidence of low back pain and the onset of radicular symptoms. There is currently no treatment available to prevent degeneration, annular tearing, nucleus migration, herniation and sciatica.

Similarly, emerging nucleus augmentation or replacement technologies rely on the integrity of a surgically weakened annulus fibrosus to prevent migration and extrusion or expulsion of implanted materials or devices. These materials and devices are typically targeted for patients in the early stages of disc degeneration (Galante I-III), where there is less degradation of the annulus fibrosus because of the reliance on annulus integrity for the success of these implants. However the annulus is typically compromised further in order to implant these materials and devices to the central region of the disc. Clinical data at this time suggests that implant migration and extrusion is one of the main complications to this type of treatment. High rates of extrusion have been reported for some nucleus replacements, 10% for the device with the most clinical experience and 20-33% for another. A need therefore exists for a method for resisting annulus tearing after or at the same time of implantation of a nucleus augmentation or nucleus replacement devices. Normal physiological loading can displace, extrude or expulse devices and materials implanted into the center, nucleus region of the intervertebral disc. Consequently, a treatment capable of improving annulus tear resistance could be useful both to prevent eminent disc protrusions and as an adjunct to a disc augmentation or nucleus replacement procedure.

Stress intensification due to tissue removal can be expected to decrease fatigue resistance in the joint tissues, leading to accelerated degradation. An example of this type of accelerated joint tissue degradation is the mechanical degradation of collagenous tissue which subsequently occurs after spinal decompression surgery. Progressive spinal degradation can also occur after surgical bone removal, with or without removal of part of the intervertebral disc as is performed in a discectomy procedure. With surgical removal of bone, disc and other connective tissues, the spinal segment can experience elevated tissue stresses due to normal physiologic loading. Discectomy procedures, in particular, have been shown to increase the neutral zone, a common parameter used to quantify the degree of spinal joint instability (Chuang and Hedman, 2007). Spinal joint instability is thought to lead to accelerated tissue degeneration and appearance of clinical symptoms. While the overall success rate of lumbar discectomy is favorable, biomechanical investigation (Goel, 1985; 1986) and long-term clinical results (Kotilainen, 1993; 1998) suggest altered kinematic behavior and degenerative changes to the lumbar spine associated with significant loss of nucleus material and disc height, including the potential for lumbar instability. Currently, no treatments are available to aide in the prevention of instability and the subsequent degeneration following discectomy or other decompression surgeries. It is herein suggested, then, that increased crosslinking following or during posterior decompression surgery would result in enhanced biomechanical properties of the intervertebral joint and a prevention or reduction of joint instability and subsequent degeneration.

Spinal deformities following vertebral fractures including kyphotic deformities following vertebral compression fractures are sometimes treated by injecting a cement-like material into the intravertebral space (vertebroplasty) sometimes following a vertebral height restoration procedure to reduce the deformity (kyphoplasty). A complementary procedure to increase the tension band restraint by increasing and improving elastic characteristics of the tensile side of the affected discs would also be beneficial in preventing the incidence of deformity as well as the progression of the deformity. Improvement of the tension band characteristics in this way stabilizes the spinal column and is a means of internal, natural bracing.

A need therefore remains for a method for improving the resistance of collagenous tissues in the human body to fatigue and for otherwise reducing the mechanical degradation of human collagenous tissues, in particular, the posterior annulus region of the intervertebral disc. In addition, a need exists to increase resistance to scoliotic curve progression and other progressive spinal deformities by treatment of appropriate regions on the tensile side (convex) of affected discs and to improve permeability, particularly the hydraulic and macromolecular permeability and diffusivity of the outer region of the disc, but also throughout the disc annulus in whole or in part and the cartilaginous endplates of the disc, the flow of nutrition, such as glucose and other nutritional macromolecules, to cells in the annulus and in the central portion of the disc, and the flow of waste products from the cells.

II. Next

NEXT (Nonsurgical EXogenous crosslink Therapy) is an injectable, biomimetic therapeutic that augments the human body's own natural response to mitigate instability and degradation of the spinal disc. The NEXT device immediately stabilizes the spinal disc reducing the pain of the patient while preventing ongoing deformity or degradation without the costs and risks associated with surgery. The procedure can be performed on an outpatient basis and could potentially be completed with just one injection treatment. Another advantage in using NEXT is that it can be administered to the patient earlier in the onset of DDD when pain and symptoms of lower back pain first present themselves; in contrast to the more traditional treatment progression where the treatment or surgery is delayed until the patient can no longer manage their daily lives due to increasing lower back pain. It is commonly known that 19 out of 20 patients elect not to pursue surgery because of the associated risks despite episodes of pain and lost work caused by debilitating DDD. The present inventors' laboratory and small animal testing to date has demonstrated that NEXT is an effective and safe treatment for a wide variety of painful spinal conditions.

III. Crosslinking Agents

The present invention addresses the use of particular crosslinking agents. In general, the crosslinking agent will be effective at crosslinking of collagenous material. When used in a cross-linking reagent, an effective crosslinker is one that increases the number of crosslinks in the collagenous tissue when the crosslinker is brought into contact with a portion of the collagenous tissue. An effective crosslinker improves the fatigue resistance of the treated tissue, reduces material property degradation resulting from repetitive physiologic loading, increases resistance to tissue tearing, resists progressive deformity, increases hydraulic permeability of the tissue, or reduces the increase of viscoelastic properties of the treated tissue due to deformity or fatigue loading. Likewise, an effective crosslinker may reduce the decrease in elastic-plastic properties due to fatigue loading of the treated tissue. In accordance with the invention, this method would utilize specific formulations of crosslinking reagents as discussed below.

The present invention also contemplates the combination of crosslinkers. Such combinations would include 2, 3, 4, 5 or more crosslinkers, including the following

|    | MG | GP | PA | TG | LT | DT |
|----|----|----|----|----|----|----|
| MG |    | X  | X  | X  | X  | X  |
| GP | X  |    | X  | X  | X  | X  |
| PA | X  | X  |    | X  | X  | X  |
| TG | X  | X  | X  |    | X  | X  |
| LT | X  | X  | X  | X  |    | X  |
| DT | X  | X  | X  | X  | X  |    |

MG—methylglyoxal,
GP—genipin,
PA—proanthrocyanidin,
TG—transglutaminase,
LT—L-threose;
DT—D-threose;
X indicates combination of the two interesecting agents.

A. Methylglyoxyl

Methylglyoxyl has been shown to increase the number of non-enzymatic glycation produced crosslinks (similar to naturally-produced crosslinks; pentosidine is one example).

B. Genipin

Genipin is an aglycone derived from an iridoid glycoside called genipiside present in fruit of *Gardenia jasmindides* Ellis. Genipin is an excellent natural cross-linker for proteins, collagen, gelatin, and chitosan cross-linking. It has a low acute toxicity, with $LD_{50}$ i.v. 382 mg/kg in mice, therefore, much less toxic than glutaraldehyde and many other commonly used synthetic cross-linking regents. It is also used for pharmaceutical purposes as a herbal remedy for its other biological effects such as its choleretic action for liver diseases control.

C. Proanthrocyanidin

Proanthrocyanidins are included in the pycnogenols, a plant polyphenol chemical group, whose physical, chemical and biological properties have been studied in numerous works (see Masquelier et al., 1979). From the biological point of view, proanthrocyanidins are characterized as plant polyphenols and noted for their lack of toxicity (see U.S. Pat. No. 3,436,407), having been used in therapeutic treatments for 30 years and shown no propensity for toxicity. Non-teratogenic, non-mutagenic, they are also non-antigenic per se and stable. Grape seed extract and pine bark extract are two of the most potent sources of proanthrocyanidins.

The bioavailability in warm blooded animals, which is related to the solubility in water, has been demonstrated by the oral administration of $^{14}C$ marked radioactive proanthocyanidins to rats and mice (Laparra et al., 1977). Thus, the fixing rate, the plasmatic half-life and the nature of the privileged sites where the proanthrocyanidins are fixed in the organism can be defined. It is the intact molecules which are involved during these measurements, since no rejection of $^{14}CO_2$ is detected in the air expired at the time when the animals are sacrificed.

In man, after the ingestion of 150 mg of pine bark extract in the form of capsules, in the following hour the presence of proanthocyanidins can be found in the saliva. The saliva gives a positive Bate-Smith reaction which implies the secretion of non-modified proanthocyanidins. This passing into the saliva thus proves the bioavailibility of proanthocyanidins in the human species. Non-antigenic, proanthocyanidins may, however, be detected also in the biological liquids and tissues by an immunological reaction.

D. Transglutaminase

Transglutaminases are a family of enzymes that catalyze the formation of a covalent bond between a free amine group (e.g., protein- or peptide-bound lysine) and the gamma-carboxamide group of protein- or peptide-bound glutamine. Bonds formed by transglutaminase exhibit high resistance to proteolytic degradation. Transglutaminases were first described in 1959. The exact biochemical activity of transglutaminases was discovered in blood coagulation protein factor XIII in 1968. In particular, the invention utilizes tissue transglutaminase which is a type II transglutaminase. Other transglutaminase such as type I, type III, factor XIII and micobial transglutaminases could also be used for the purposes of this invention E.  1-Ethyl-3-[3-dimethylaminopropyl]carbodiimide (EDC)

EDC (1-ethyl-3-[3-dimethylaminopropyl]carbodiimide hydrochloride) is a water soluble carbodiimide which is typically employed in the 4.0-6.0 pH range. It is generally used as a carboxyl activating agent for the coupling of primary amines to yield amide bonds. Additionally, EDC can also be used to activate phosphate groups. Common uses for this carbodiimide include peptide synthesis, protein crosslinking to nucleic acids and preparation of immunoconjugates. EDC is often used in combination with N-hydroxysuccinimide (NHS) or sulfo-NHS to increase coupling efficiency or create a stable amine-reactive product. Nakajima and Ikada, 1955; Skotnicki, 1944.

F. L- or D-threose

Threose is a tetrose carbohydrate with chemical formula $C_4H_8O_4$. It has one aldehyde group and so is part of the aldose family. It exists in both D- and L-stereoisomers.

G. Agent Concentrations

In vitro biochemical experiments have suggested effective working concentrations for various crosslinkers once in contact with the target tissue. It is important to note that due to other considerations, such as potential dilution of the crosslinker during clinical use, the concentration of the reagent in the final formulation may be higher than those stated below. In particular, the crosslinking reagent contains one of the following ranges of agent concentrations or a combination of agent concentrations: at least 1 U/ml) of transglutaminase, at least 2.5 mM genipin, at least 0.025% proanthrocyanidin, at least 1 mM EDC, at least 100 mM ribose, at least 25 mM L-Threose, at least 2.5 mM methylglyoxal, at least 2.5 mM glyoxal, at least 0.001% lysyl oxidase, preferably in a 0.1 M urea solution. In the case of non-enzymatic agents such as ribose, L-Threose, methylglyoxal and glyoxal, the reagent may contain an oxidant such as hydrogen peroxide, or sodium percarbonate, or sodium borate, or an amino acid hydroperoxide, or perborate, or a buffer such as sodium bicarbonate or phosphate, or some combination of oxidants and buffers. In the case of enzymatic crosslinking agents, the crosslinking reagent may also contain, in addition to the enzyme, a peptide containing amino acids that can be crosslinked by the enzyme. These peptides would provide additional substrate for the cross-linking reaction and facilitate the crosslinking of residues which would not normally be in close enough proximity to react, thereby increasing the number of crosslinks formed. In the case of LO, the peptide would need to contain at least two lysine residues. In the case of TG, the peptide could contain at least two lysine residues, or at least two glutamine residues or at least one lysine and one glutamine residue. More than one crosslinking agent may be used.

IV. Formulations

The crosslinking reagent may include a carrier medium in addition to the crosslinking agent. The crosslinking agent may be dissolved or suspended in the carrier medium to form the crosslinking reagent. In one embodiment, a crosslinking agent is dissolved in a non-cytotoxic and biocompatible carrier medium. The carrier medium is required to be substantially non-cytotoxic in order to mediate the contact of the crosslinking agent to tissues in the living human body without substantial damage to the tissue or surrounding tissue. In particular, the carrier medium chosen is water, and more specifically, a saline solution. The pH of the carrier medium is adjusted to a level sufficient to promote crosslinking without being harmful to the tissue. Even more particularly, the carrier medium is buffered. This is particularly important since it has been shown that the pH of a disc undergoing DDD is highly acidic due to the production of lactic acid by glycolysis in this anaerobic environment (Buckwalter, 1995; Kitano T, Clinical Orthopaedics and Related Research, 1993; Horner and Urban, 2001; Urban et al., 2004). A buffer would allow an optimal pH to be transiently maintained to promote crosslinking during the treatment. In one embodiment of the present invention, the carrier medium is a phosphate buffered saline (PBS). In another embodiment of the present invention, the carrier is a semisolid or liquid formulation, and may contain encapsulated nanoparticles designed to provide a sustained release of the cross-linking agent or agents after administration into or onto the tissue.

In addition, the carrier medium may also contain other ingredients that promote the crosslinking reaction.

When the crosslinking agent is dissolved in a carrier medium, the concentration of the crosslinking agent in the carrier medium is not particularly limited. The concentration may be in any amount effective to increase the crosslinking of the tissue while at the same time remaining substantially noncytotoxic.

A. Buffers

In general, any buffer whose pKa is suitable to maintain the buffering capacity of the formulation before and after administration at a pH level that is capable of sustaining crosslinking, and which is not substantially toxic to the organism, can be considered to be suitable for the purposes of this application. The following are examples of various buffers that can be utilized in accordance with the present invention.

i. EPPS

EPPS, or 4-(2-hydroxyethyl)-1-piperazinepropanesulfonic acid (also HEPPS), is closely related to the common buffer HEPES. It is a physiologic buffer of the formula $C_9H_{20}N_2O_4S$ with a FW of 252.33. The pKa is 8 and the useful pH range is 7.3-8.7.

ii. Tris

Tris is an abbreviation of the organic compound known as tris(hydroxymethyl)aminomethane, with the formula $(HOCH_2)_3CNH_2$. Tris is extensively used in biochemistry and molecular biology. In biochemistry, tris is widely used as a component of buffer solutions, such as in TAE and TBE buffer, especially for solutions of nucleic acids. It contains a primary amine and thus undergoes the reactions associated with typical amines, e.g. condensations with aldehydes.

Tris has a pKa of 8.3 (at 20° C.), which implies that the buffer has an effective pH range between 7.0 and 9.2. Being slightly basic, tris forms an effective buffer for slightly basic solutions, which keeps DNA deprotonated and soluble in water. Tris is commonly combined with EDTA to make "TE buffer" for stabilization and storage of DNA. EDTA binds to magnesium ($Mg^{2+}$), which is a co-factor for many DNA-modifying enzymes. More importantly, however, EDTA has a stronger affinity for iron ions, which are often trace contaminants in magnesium, and which can react with DNA. Thus only a small amount of EDTA is typically added, most of which binds to magnesium and reduces the effective magnesium concentration, but it also functions to protect the DNA from being cut by iron. Tris is also used clinically in the treatment of blood acidosis.

iii. MES

MES is the common name for the compound 2-(N-morpholino)ethanesulfonic acid. Its chemical structure contains a morpholine ring. It has a molecular weight of 195.2 and the chemical formula is $C_6H_{13}NO_4S$. Synonyms include: 2-morpholinoethanesulfonic acid; 2-(4-morpholino)ethanesulfonic acid; 2-(N-morpholino)ethanesulfonic acid; 2-(4-morpholino)ethanesulfonic acid; MES; MES hydrate; and morpholine-4-ethanesulfonic acid hydrate. MOPS is a similar pH buffering compound which contains a propanesulfonic moiety instead of an ethanesulfonic one.

MES is used as a buffering agent in biology and biochemistry. It was developed as one of Good's buffers in the 1960's, with pKa value of 6.15. These buffers were developed with the following criteria in mind: midrange pKa, maximum water solubility and minimum solubility in all other solvents, minimal salt effects, minimal change in pK with temperature, chemically and enzymatically stable, minimal absorption in visible or UV spectral range and reasonably easily synthesized. The melting point is approx. 300° C. It is soluble up to 2M in water. It is also useful as a non-coordinating buffer in chemistry involving metal ions, as many common buffers (e.g., phosphate and acetate) readily form coordination complexes.

iv Phosphate Salts

Phosphate salts (normally of sodium or potassium) are commonly used, biocompatible buffers. Phospate has three pKas; 2.2, 6.8 and 12.4. The pKa at 6.8 is used to buffer solutions in a physiological range.

B. pH Adjustments

The inclusion of the buffering agent is in itself not sufficient to produce an optimal formulation. The pH of the formulation following addition of the buffer is adjusted to the desired level with either an acid or base. In some cases the buffering species may also play a role in enhancing the crosslinking reaction.

V. Additional Agents

A. Enhancers

The present invention contemplates crosslinking compositions, as discussed above, further including enhancers of crosslinking. The inventors propose two classes of enhancer: phosphate ions and borohydride. Phosphate and borohydride ions may be provided by virtue of the corresponding sodium or other metal salts. Phosphate will find particular utility with genipin and methylglyoxal. Borohydride ions, at least with methylglyoxal, are useful in a range of 1-5 mM, 1.5-5 mM, and optimal at about 1.5 mM.

The action of borohydride is to reduce unstable Schiff's base intermediates during the methylglyoxal crosslinking reaction. Other reducing agents may also be used at levels that enhance crosslinking but are not so high as to break endogenous collagen crosslinks or otherwise damage the tissue. It has been suggested that phosphate can enhance glycosylation (and therefore Maillard-type crosslinking) by interacting with the protein and then accepting protons from an crosslinking intermediate (Watkins et al., 1987). Therefore, molecules with similar structures such as borates, perborates, carbonates, percarbonates, nitrates, sulfates, sulfites, persulphates, sulfonic acids, chlorates, perchlorates, pyrophosphates, triphosphates and poly phosphates might also function to promote crosslinking via similar mechanisms.

As mentioned above, some buffering agents may also enhance crosslinking not only by maintaining the pH of the formulation but also by chemical means.

B. Surfactants

The present invention may benefit, additionally, from the incorporation of surfactants into the crosslinking compositions. Surfactants are substances possessing both a hydrophilic group and a hydrophobic group. A surfactant which dissociates in water and releases cation and anion (or zwitterions) is termed ionic (cationic, anionic, zwitterionic) surfactant. A surfactant which does not dissociate is called a non-ionic surfactant.

The surfactant may be a non-ionic surfactant, such as a member of the Tween series of surfactants (polysorbates), a member of the Triton series of surfactants, a member of the Brij series of surfactants, polyethylene glycol, an alkyl mono-, di-, tri- or poly-ethylene glycol, an alkylated sugar, Brij) family surfactants, Nonidet™ surfactants, SODOSIL® family surfactants, saponin, Tergitol® family surfactants, as well as others.

Alternatively, the surfactants may be anionic surfactants, such as an alkyl sulfonate such as SDS, sodium cholate, sodium deoxycholate, an alkyl benzene sulfonate, N-lauroyl-sarcosine, or a fatty acid salt.

VI. Disease States and Delivery

In accordance with the present invention, the crosslinking reagent is brought into contact with a portion of a native, non-denatured collagenous tissue. As used herein, collagenous tissue is defined to be a structural or load supporting tissue in the body comprised of a substantial amount of collagen. Examples would include intervertebral disc, articular cartilage, meniscus, fibrocartilage, ligament, tendon, bone, and skin. In general, the portion of the collagenous tissue to be brought into contact with the crosslinking reagent is the portion of the tissue that is subject to loading. Further, where at least some degradation of the collagenous tissue has occurred, the portion of the tissue to be contacted with the crosslinking reagent is at least the portion of the tissue that has been degraded or deformed. The entire portion that is subject to loading or the entire portion that is degraded or deformed may be contacted with the crosslinking reagent. Further, the tissue adjacent the portion of collagenous tissue subject to the loading may also be contacted with the crosslinking reagent. Delivery of the crosslinking agent may be facilitated by the use of fluoroscopy to guide correct placement of the needle. In addition contrast agents, which may be present in the formulation itself or mixed with it prior to use, may be included to visualize the delivery of the crosslinker and to ensure full coverage of the tissue.

The collagenous tissues that are particularly susceptible for use in accordance with the present invention include intervertebral discs and articular cartilage or fibrocartilage such as knee meniscus. Where the collagenous tissue is an intervertebral disc, the portion of the intervertebral disc that is contacted by the crosslinking reagent is the posterior and posterolateral annulus fibrosis. Contact to the entire intervertebral disc may provide additional therapeutic effect.

The selected portion of the collagenous tissue must be contacted with an effective amount of the non-toxic crosslinking reagent. An "effective amount" is an amount of crosslinking reagent sufficient to have a mechanical effect on the portion of the tissue treated. Specifically, an "effective amount" of the crosslinking reagent is an amount sufficient to improve the fatigue resistance of the treated tissue, reduce material property degradation resulting from repetitive physiologic loading, increase joint stability, increases resistance to tissue tearing, increases resistance to deforming forces, increases hydraulic permeability of the tissue, or reduce the increase of viscoelastic properties of the treated tissue due to fatigue loading, or reduce the decrease of elastic-plastic properties of the treated tissue due to fatigue loading. An effective amount may be determined in accordance with the viscoelastic testing, elastic-plastic testing, deformity resistance testing, tear testing, stability testing, and/or hydraulic permeability testing.

The method of the present invention includes contacting at least a portion of the collagenous tissue with an effective amount of the crosslinking reagent. The contact may be effected in a number of ways. The contacting of collagenous tissue may be effected by a means for minimally invasive delivery of the non-cytotoxic crosslinking reagent. The contact between the tissue and the crosslinking reagent may be effected by injections directly into the select tissue using a needle. The contact between the tissue and the crosslinking reagent may be effected by injections from a single or minimum number of injection locations. An amount of crosslinking solution may be injected directly into the targeted tissue using a needle and a syringe. A sufficient number of injections should be made along the portion of the tissue to be treated so that complete coverage of the portion of the collagenous tissue to be treated is achieved.

Alternatively, contact between the tissue and the crosslinking reagent is effected by placement of a time-release delivery system directly into or onto the target tissue. One time-released delivery system that may be used is a treated membrane or patch. A reagent-containing patch may be rolled into a cylinder and inserted percutaneously through a cannula to the tissue sight, unrolled and using a biological adhesive or resorbable fixation device (sutures or tacks) be attached to the periphery of the targeted tissue.

Another time-released delivery system that may be used is a liquid, gel, cream or ointment. Such biocompatible, carriers may be applied to the exterior of the targeted tissue. Alternatively, such time-released delivery systems could be applied to the interior of the tissue by, for example, injection. Contact also may be effected by soaking or spraying, such as intracapsular soaking or spraying, in which an amount of crosslinking solutions could be injected into a capsular or synovial pouch.

A form of mechanical degradation of load supporting collagenous tissues includes tearing of the tissues. In a second embodiment, the present invention relates to methods and devices for the treatment of fibrous collagenous tissues and surrounding tissues by directly contacting the select tissues with a crosslinking reagent to improve the resistance to tearing of the tissue. The collagenous tissues that are particularly susceptible to tearing include intervertebral discs and articular cartilage or fibrocartilage such as knee meniscus. Where the collagenous tissue is an intervertebral disc, the portion of the intervertebral disc that is contacted by the crosslinking reagent may be the posterior and posterolateral annulus fibrosis. Where the treated tissues include the intervertebral disc, the present invention also relates to methods and devices for prevention of disc herniation. The present invention could be used in a conservative approach to prevent tearing of disc tissue, in particular, radial tearing of the annulus fibrosus leading to expulsion of nucleus pulposus materials.

One aspect of this embodiment provides a method of improving the tear resistance of native intervertebral disc tissue prior to a disc herniation by contacting the tissue with a non-toxic crosslinking reagent. This embodiment also provides a method of improving tear resistance where a herniation has already occurred by contacting the tissue with non-toxic crosslinking reagents. Another aspect of this embodiment provides a method of improving the tear resistance of native knee meniscus tissue subsequent to a partial tearing of the meniscus. This embodiment also provides a method of improving tear resistance of native knee meniscus tissues prior to tearing of the meniscus.

In this embodiment, an effective amount of crosslinking reagent is an amount that creates crosslinks in the target tissue, such as in regions of the tissue where the majority of tissue tearing is known to occur. In the case of intervertebral disc tissues, the treatment may be on the posterior and posterolateral regions of the annulus fibrosus such that the resistance to tearing is increased for the prevention of disc herniation. In the case of knee meniscus tissues, the tissue may be treated in the region of existing partial tears and to surrounding meniscal tissues. The knee meniscal tissue may also be treated in its entirety. If only the medial meniscus or only the lateral meniscus is affected, both the medial and lateral meniscus can be treated. If the meniscal tissues in one knee is affected, the crosslinking treatment could also be made on the meniscal tissues in the contralateral knee.

A method according to this embodiment may be use a minimally invasive delivery of the non-cytotoxic crosslinking reagents, such as a series of injections, to the affected discs or knee meniscus or cartilaginous or bony or capsular or ligamentous tissues in order to contact the appropriate tissue with appropriate concentrations of non-toxic crosslinking reagents. This aspect of the present invention is used in a conservative approach to prevent ongoing tearing and degeneration of these tissues and in the case of the intervertebral disc, to prevent subsequent herniations of the disc.

A treatment method according to this embodiment may incorporate a means for minimally invasive delivery of the non-cytotoxic crosslinking reagent such as placement of a time-release delivery system such as an imbedded pellet, time release capsule, gel, ointment, cream, semisolid or liquid, or a treated membrane or patch directly into or onto the target tissue. Additional, guidable, arthroscopic-types of devices may be developed to facilitate application of the reagents to appropriate areas on the intervertebral discs or knee meniscus or adjacent cartilaginous, bony, capsular or ligamentous tissues. This aspect of the present invention is used in a conservative approach to prevent ongoing tearing and degeneration of these tissues and in the case of the intervertebral disc, to prevent subsequent herniations of the disc.

In a third embodiment, the present invention relates to methods and devices for the treatment of intervertebral discs subsequent to or in combination with a nucleus replacement or nucleus augmentation type procedure, and to prevention of extrusion or expulsion of the implanted materials and/or devices. Nucleus pulposus replacement or augmentation technologies rely on the integrity of a surgically weakened annulus fibrosus to prevent migration and extrusion or expulsion of implanted materials or devices. The present invention could be used for resisting annulus tearing after or at the same time of implantation of a nucleus augmentation or nucleus replacement devices. The present invention provides methods and devices such that an injectable nucleus replacement or augmentation materials could be combined with crosslinking reagents to prevent extrusion of the implanted materials. This embodiment would involve delivery of the crosslinking reagents to the central region of the disc and would create an inside-out progression of crosslinking, with the more central annulus tissues being in direct contact with the crosslinking reagents. Alternatively, the present invention provides for a separate crosslinking treatment of the annulus performed at approximately the same time as a nucleus replacement or augmentation procedure. Alternatively, the present invention provides for a crosslinking treatment of the annulus performed subsequent to a nucleus replacement or augmentation procedure. Also, this invention provides for the treatment of the annulus preceding the implantation of the nucleus materials or devices.

In this embodiment, an effective amount of crosslinking reagent is an amount that creates crosslinks in the target tissue, such as on all of the annulus surrounding a nucleus replacement implant material or device, also such as on the region surrounding the defect formed by surgical introduction of the implant, also such as on the surrounding tissues including the cartilaginous vertebral endplates and capsular and ligamentous tissues, such that the annulus resistance to tearing is increased.

In particular, a method according to this embodiment uses a minimally invasive delivery of the non-cytotoxic crosslinking reagents. A minimally invasive delivery includes a series of injections, to the target tissues of or adjacent to discs which have received or are receiving or will receive a nucleus replacement or augmentation procedure, in order to contact the appropriate tissue with appropriate concentrations of non-toxic crosslinking reagents. This aspect of the present invention is used in a conservative approach to prevent further tearing of the annulus prior to or following implantation of a nucleus replacement device or materials, and to prevent migration or expulsion or extrusion of implant materials or devices.

Another minimally invasive delivery includes placement of a time-release delivery system such as an imbedded pellet, time release capsule, gel, ointment, cream, semisolid or liquid, or a treated membrane or patch directly into or onto the target tissue. Additional, guidable, arthroscopic-types of devices may be developed to facilitate application of the reagents to appropriate areas on the intervertebral discs or adjacent cartilaginous, bony, capsular or ligamentous tissues. This aspect of the present invention is used in a conservative approach to prevent further tearing of the annulus prior to or following implantation of a nucleus replacement device or materials, and to prevent migration or expulsion or extrusion of implant materials or devices.

A fourth embodiment of the present invention provides methods and devices for enhancing the body's own efforts to stabilize discs in scoliotic spines or other mechanically insufficient or potentially deforming or deforming spines such as listhetic spines, (which contains at least one partially slipped disc), those following a neural decompression procedure such as a laminectomy or subsequent to installation of spinal instrumentation, by increasing collagen crosslinks. A form of mechanical degradation to intervertebral discs occurs as a part of progressive curvature of the spine. For example, spinal curve progression in scoliosis involves increased unloaded curvature of segments of the spine. With this increased curvature there is an associated increase of gravity-induced bending moments on the spine, acting to change the stress environments of the tissues leading to an increase of the curvature of these already affected joints. Although it may also be considered as a sustained or static type of load, with a period of loading equal to the period of upright activity during any given day, the "repetitive" or fatigue loading associated with scoliosis curve progression would be comprised of the daily gravitational loads and passive and active muscle and connective tissue actuated loads and their effective moments applied to the spinal column over the course of many days. With increasing deformity, the deforming moments are increased as the "moment arm"—the distance through which the applied forces generate moments—increases. The fundamental rationale behind scoliotic bracing, and bracing for other spinal deformities is to resist these deforming forces and moments, affecting the loading environment of the cells in the bones and connective tissue, and to resist curve progression. The present invention could be used in a conservative approach to prevent ongoing curvature of spines and as an adjunct to corrective surgery to stabilize the remaining discs against loss of correction. It could be used alone or with external bracing.

One aspect of this embodiment provides a method of improving the stability of intervertebral disc tissue in scoliotic or other mechanically insufficient or potentially deforming or deforming spines, such as spondilolisthesis ("slipped discs"), aiding the cell's efforts to increase collagen crosslinks on the tensile (convex) side of the curves and slips, by contacting the tissue with one or more of the non-toxic crosslinking reagents.

In this embodiment, an effective amount of crosslinking reagent is an amount that creates crosslinks in the target tissue, such as on the convex side of discs at or near the apex or apexes of a spinal curve or of a potential spinal curve, such that at least one of the following effects are achieved: deformity-increasing bending hysteresis is decreased, elastic energy storage and return is increased, and the deformity-increasing bending stiffness is increased.

In particular, a method according to this embodiment uses a minimally invasive delivery of the non-cytotoxic crosslinking reagents, such as a series of injections, to the tensile (convex) sides of affected discs and adjacent bones, capsular or ligamentous tissues in order to contact the appropriate tissue with appropriate concentrations of non-toxic crosslinking reagents. The appropriate locations for injection are determined using three-dimensional reconstructions of the affected tissues as is possible existing technology, and combining these reconstructions with an algorithm to recommend the optimum placement of these reagents so as to affect the greatest possible restraint of ongoing spinal curve progression. These three-dimensional depictions of locations for crosslinker application may best be created with custom computer software that incorporates medical images of the patient, and may be displayed on a computer driven display device such as a lap-top computer or a devoted device. This aspect of the present invention is used in a conservative approach to prevent ongoing curvature of scoliotic and other progressively deforming spines and as an adjunct to corrective surgery to stabilize the remaining discs against loss of correction. It is used alone or with external bracing.

In particular, a treatment method according to this embodiment incorporates a means for minimally invasive delivery of the non-cytotoxic crosslinking reagent such as placement of a time-release delivery system such as an imbedded pellet, time release capsule, gel, ointment, cream, semisolid or liquid, or a treated membrane or patch directly into or onto the target tissue. Additional, guidable, arthroscopic-types of devices may be developed to facilitate application of the reagents to appropriate areas on the intervertebral discs or adjacent bony, capsular or ligamentous tissues. This aspect of the present invention is used in a conservative approach to prevent ongoing curvature of spines and as an adjunct to corrective surgery to stabilize the remaining discs against loss of correction. It is used alone or with external bracing.

Decreased diffusion into the central portion of the intervertebral disc is strongly related to the loss of cell function in the disc and disc degeneration. This loss of diffusion capabilities affects both the cartilaginous endplates of the disc (above and below) and the outer region of the disc, the annulus fibrosus. A fifth embodiment of the present invention provides methods and devices for increasing load supporting collagenous tissue permeability and the flow of nutrition by increasing collagen crosslinks by using one or more of the crosslinking reagents. The present invention increases changes in the hydration of various regions of an intervertebral disc in a way that demonstrates an increased fluid flow into and out of the central region, or nucleus pulposus, of the intervertebral disc afforded by increased crosslinking of the outer region of the disc, the annulus fibrosus and/or the cartilaginous endplates. The changes effected by crosslinking increase the hydraulic permeability of the outer regions of the disc and increase solute transport to and from the central regions of the disc. Also, the present invention increases hydraulic permeability of the outer regions of the knee meniscus tissues and increases solute transport to and from the inner regions of the knee meniscus.

One aspect of this embodiment provides a method to increase the permeability of the outer region of the intervertebral disc, the annulus fibrosus and/or the cartilaginous endplates, and by this improve the fluid flux to and from the central region, or nucleus pulposus, of an intervertebral disc by increasing collagen crosslinks.

A second aspect of this embodiment provides a method to increase the outer disc permeability and increase fluid flux to the central region of the disc to increase the flow of nutrients to the cells in the central region, while also increasing the flow of cell waste products and degraded matrix molecules from the central region of the disc, by increasing collagen crosslinks.

A third aspect of this embodiment provides a method to increase the biological viability of cells, native or implanted, or the effectiveness of cell stimulating agents such as cytokines and growth factors in the central region of the intervertebral disc by increasing collagen crosslinks. This embodiment provides a method for improving flow of nutrients to the central region of the intervertebral disc while also improving outflow of waste products from this central region. This improvement of flow is brought about by increased permeability of the outer region of the disc produced by application of crosslinking reagents to this outer region. This embodiment also provides a method for improving flow of nutrients to the central region of the knee meniscus while also improving outflow of waste products from this central region.

Methods according to this embodiment use a minimally invasive delivery of the non-cytotoxic crosslinking reagents, such as a series of injections, or the placement of a time-release delivery system such as an imbedded pellet, time release capsule, gel, ointment, cream, semisolid or liquid, or a treated membrane or patch directly into or onto the target tissue. Additional, guidable, arthroscopic-types of devices may be developed to facilitate application of the reagents to appropriate target areas. These delivery methods are used in a conservative approach to increase the fluid flow, solute transport, nutrient supply, and waste removal to the central region of the disc or meniscus by crosslinking treatment of the outer region, or annulus of the disc or meniscus. These delivery methods function as an essential adjunct to tissue engineering treatments of the intervertebral disc to improve the viability of the implanted or otherwise treated cells and to effect an increase in the biological activity of the disc or meniscus. Tissue engineering treatments and cell or cytokine based methods may include any of the following: implantation of stem cells of any derivation (autogenous or autologous, embryonic or non-embryonic, muscle derived, adipose derived, etc.), gene-therapy delivery of growth factors, implantation of matrices with attached growth factors, direct application of growth factors, implantation of transplanted tissues or cells, implantation of xenograft tissues or cells, implantation of differentiated cells derived from stem cells, to promote increased biological activity in the disc or meniscus. In addition, these delivery methods will be used where no tissue engineering type of treatment is applied with the aim to increase diffusion to the central region of the disc, the nucleus pulposus, or to the central region of the knee meniscus.

It should be noted that the methods and compositions treated herein are not required to permanently improve the resistance of collagenous tissues in the human body to mechanical degradation, or to permanently increase joint stability, or to permanently increase resistance to tissue tearing, or to permanently increase tissue permeability, or to permanently increase resistance to deformity. Assuming that a person experiences 2 to 20 upright, forward flexion bends per day, the increased resistance to fatigue, instability, deformity and tearing and the increase in permeability associated with contact of the collagenous tissue with the crosslinking reagent, may, over the course of time, decrease. The increased resistance to fatigue, instability, deformity and tearing and the increased permeability may last for a period of several months to several years without physiologic mechanical degradation. Under such circumstance, the described treatment can be repeated at the time periods sufficient to maintain an increased resistance to fatigue, instability, deformity and tearing and increased permeability. Using the assumption identified above, the contacting may be repeated periodically to maintain the increased resistance to fatigue, instability, deformity and tearing and increased permeability. For some treatment, the time between contacting is estimated to correspond to approximately 1 year for some individuals. Therefore, with either a single treatment or with repeated injections/treatments, the method of the present invention minimizes mechanical degradation of the collagenous tissue over an extended period of time.

Another aspect of the present invention relates to using the aforementioned crosslinking agents as a device or "reagent and application tray" for improving the stabilization of intervertebral discs, for improving the resistance of collagenous tissue to mechanical degradation, for increasing the permeability of the intervertebral disc, for improving the fluid flux to and from the intervertebral disc, and for increasing the biological viability of cells in the intervertebral disc. The "reagent and application tray" is sterile and contained within a sterile package. All of the necessary and appropriate and pre-measured reagents and solvents (or pre-formulated reagents) and disposable delivery devices are packaged together in an external package that contains a suitable wrapped sterile "reagent and application tray." This sterile tray containing the reagents and solvents (or pre-formulated reagents), and delivery devices is contained in a plastic enclosure that is sterile on the inside surface. This tray will be made available separate from the computer hardware and software package needed to suggest appropriate application positions.

VII. EXAMPLES

The following examples are included to demonstrate specific embodiments of the invention. It should be appreciated by those of skill in the art that the techniques disclosed in the examples which follow represent techniques discovered by the inventors to function well in the practice of the invention, and thus can be considered to constitute particular modes for its practice. However, those of skill in the art should, in light of the present disclosure, appreciate that many changes can be made in the specific embodiments which are disclosed and still obtain a like or similar result without departing from the spirit and scope of the invention.

Examples 1 & 2

Viscoelastic and Elastic-Plastic Degradation Resistance

Thirty-three lumbar intervertebral joints were obtained from ten four-month-old calf spines. The intervertebral joints were arbitrarily divided into 3 groups: untreated controls-12 specimens, Genipin treatment 1 (G1)-6 specimens, and Genipin treatment 2 (G2)-13 specimens. The G1 treatment involved 72 hrs of soaking the whole specimen in PBS with a 0.033% concentration of Genipin. Similarly, the G2 treatment involved 72 hrs of soaking whole specimens in PBS with 0.33% concentration of Genipin. 0.33% Genipin in PBS is produced by dilution of 50 ml of 10×. PBS (Phosphate Buffered Saline) with distilled water by a factor of 10 to give 500 ml (500 gm) of PBS and mixing in 1.65 grams of genipin to produce the 0.33% (wt %, gm/gm) solution. Previous testing with pericardium and tendon tissue samples demonstrated the reduction of tissue swelling (osmotic influx of water into the tissue) resulting from crosslinking the tissue. Some controls were not subjected to soaking prior to fatigue testing. Others were soaked in a saline solution for 72 hrs. Water mass loss experiments were conducted to establish the equivalency of outer annulus hydration between the genipin soaked and 0.9% saline soaked controls. The selection of treatments was randomized by spine and level. The vertebral ends of the specimens were then potted in polyurethane to facilitate mechanical testing.

Indentation testing and compression/flexion fatigue cycling were carried out in the sequence presented in Table 1.

TABLE 1

Experimental protocol

| Measurement Sequence | Measurement | Location |
| --- | --- | --- |
| 1 | Stress Relaxation | Center of the Posterior Annulus |
| 2 | Hardness | Center of the Posterior Annulus |
| | 3000 Compression/Flexion Fatigue Cycles | |
| 3 | Stress Relaxation | 4 mm Lateral to Center |
| 4 | Hardness | Center of the Posterior Annulus |
| | Additional 3000 Compression/Flexion Fatigue cycles | |
| 5 | Stress Relaxation | 4 mm Lateral to Center |
| 6 | Hardness | Center of the Posterior Annulus |

At the prescribed points in the loading regimen, indentation testing was used to find viscoelastic properties as follows. Stress relaxation data was gathered by ramp loading the 3 mm diameter hemi-spherical indenter to 10 N and subsequently holding that displacement for 60 s, while recording the resulting decrease in stress, referred to as the stress relaxation. Indentation testing was also utilized to determine elastic-plastic properties by calculating a hardness index (resistance to indentation) from ramp loading data. Prior to recording hardness measurements, the tissue is repeatedly indented 10 times (60 s/cycle, to the displacement at an initial 10 N load).

This test protocol is based on two principles. First, viscoelastic effects asymptotically decrease with repeated loading. Secondly, hardness measurements are sensitive to the loading history of the tissue. However this effect becomes negligible following 10 loading cycles. In order to minimize these effects, viscoelastic data (stress relaxation) was collected from tissue that had not previously been indented. Alternately, elastic-plastic data (hardness) was collected from tissue that had been repeatedly loaded (preconditioned). In this case, repetitive indentation was intended to reduce the undesired effects of the changing viscoelastic properties, namely lack of repeatability, on hardness measurements. These testing procedures were derived from several preliminary experiments on the repeatability of the measurements with variations of loading history and location.

Following initial indentation testing, the specimen was loaded repetitively in flexion-compression at 200 N for 3000 cycles at a rate of 0.25 Hz. The load was applied perpendicularly to the transverse plane, 40 mm anterior to the mid-point of the specimen in the transverse plane. A second set of indentation testing data is then collected following fatigue cycling. This procedure was followed for two fatigue loading cycles. During all testing, the specimens were wrapped in saline wetted gauze to maintain their moisture content. Fatigue cycling and non-destructive indentation testing were carried out on an MTS 858.02 biaxial, table-top, 10 kN capacity servo-hydraulic materials test station (MTS, Eden Prairie, Minn.), with the MTS Test Star data acquisition system. Several statistical measures were calculated to evaluate the significance of the results. A nested two-way analysis of variance (ANOVA) was utilized to confirm effects due to treatment and number of fatigue cycles. Due to the non-parametric nature of the data, the Mann-Whitney non-parametric rank-sum test was used to assess the null hypotheses that the treatment did not affect: (1) the pre-cycling mechanical parameters of the tissue, or (2) the amount of change (degradation) in elastic-plastic and viscoelastic mechanical parameters due to fatigue loading. The confidence level for statistical significance was set at $p<0.05$.

Nested two-way ANOVA analysis determined that both viscoelastic (relaxation) and elastic-plastic (hardness) mechanical parameters were independently affected by fatigue cycling and by treatment type. These statistical results are presented in Table 2.

There was an initial shift downward of the relaxation curve caused by the crosslinking treatment. This would represent a beneficial effect as higher stress relaxation would be associated with more severely degraded tissue (Lee et al., 1989). The initial pre-fatigue relaxation of the G1 and G2 treatment groups were 26% and 19% less than ($p=0.009$ and $p=0.026$) the pre-fatigue relaxation of the controls respectively. There was also dramatic improvement in fatigue resistance as demonstrated by the change in relaxation after 6000 non-traumatic loading cycles. The change in relaxation due to 6000 fatigue cycles for the G2 treated discs was less than a third of the change in the controls ($p=0.044$). However, the lesser concentration of Genepin did not bring about the same improvement in fatigue resistance.

There is an initial shift upward of the hardness data caused by the G2 crosslinking treatment. This would represent a beneficial effect as loss of hardness would signal a loss of structural integrity in the tissue. The initial pre-fatigue hardness of the G2 treatment group was 17% greater than that of the control group ($p=0.026$). However this beneficial effect appears to have eroded prior to 3000 fatigue cycles and the change in hardness between 3000 and 6000 cycles is essentially the same for the two groups (G2=0.94, Control=−1.01).

TABLE 2

Results of nested two-way ANOVA analysis

| Material Property | Factor | F-Value | Probability |
|---|---|---|---|
| Stress Relaxation | Treatment | 16.060 | 1.085E−06 |
|  | Fatigue Cycling | 9.676 | 2.500E−03 |
|  | Interaction | 1.402 | 2.515E−01 |
| Hardness | Treatment | 20.023 | 6.405E−08 |
|  | Fatigue Cycling | 5.898 | 1.710E−02 |
|  | Interaction | 4.228 | 1.760E−02 |

The data presented above quantifies the elastic and viscoelastic mechanical degradation of intervertebral disc tissue due to repetitive, non-traumatic loading. The results of these experiments establish that non-toxic crosslinking reagents reduce the fatigue-related degradation of material properties in a collagenous tissue, namely, the intervertebral disc. More than a three-fold reduction in viscoelastic degradation was brought about by soaking the calf disc tissue in 0.33 g/mol concentration of genipin. The tested formulation was unable to sustain an improvement in the elastic mechanical properties (hardness) to 3000 test cycles.

Accurately estimating the length of time it would take an average person to experience a comparable amount of wear and tear on their spinal discs is difficult. Certainly, in addition to the mechanical degradation imposed by the described testing, there is the added "natural" degradation of these dead tissues due to the testing environment. The non-loaded controls showed this "natural" degradation of material properties to be insignificant. Measures were taken to minimize this natural degradation by keeping the specimens moist throughout the testing and by accelerating the loading frequency. At the same time, loading frequency was kept within physiologic limits to prevent tissue overheating. It should be noted that these measures constitute standard protocol for in vitro mechanical testing of cadaveric tissues. Assuming that a person experiences 2 to 20 upright, forward flexion bends per day, these data roughly correspond to several months to several years of physiologic mechanical degradation.

The described treatment could be repeated at the time periods represented by, for instance, 3000 fatigue cycles at this load magnitude. Using the assumption identified above, this number of cycles may be estimated to correspond to approximately 1 year for some individuals. Therefore, with either a single treatment or with repeated injections/treatments, an individual may be able to minimize mechanical degradation of their intervertebral discs over an extended period of time. Another option would involve a time-release delivery system such as a directly applied treated patch, a gel or ointment.

Example 3

Deformity Resistance

Experiments were conducted to evaluate the efficacy of applying different formulations of crosslinking reagents with known minimal cytotoxicity unilaterally to intervertebral disc annular tissue in order to affect the lateral bending stability of the tissue compared to pre-treatment. Experiments utilized 5 calf spine segments, each segment comprised of 3 lumbar intervertebral joints (motion segments), four vertebrae and the intervening 3 discs. The pedicles were cut and the posterior processes removed. The segments were randomly divided into a 0.33% by weight genipin crosslinked group, a 0.5% genipin group, a 0.66% genipin group, and a 0.66% genipin plus 0.1% proanthocyanidin group. Each group consisted of one 3 motion segment specimen. Each pre-treated spine served as its own control. Repeated testing was performed on some untreated and treated specimens to determine repeatability of the measurements. Additional appropriate concentrations and combinations of known minimally cytotoxic crosslinking reagents will be chosen based on the documented cytotoxicity of a particular tissue. In this regard it is expected that sugar solutions (such as ribose and 1-threose), byproducts of metabolism (such as methylglyoxal and glyoxal) and naturally occurring enzymes (such as lysyl oxidase and transglutaminase) will be essentially non-cytotoxic. Similar testing will be conducted on fresh-non-frozen animal tissue with appropriate sterilization procedures and antibiotics to prevent tissue degradation. Sugar solutions will be injected unilaterally into fresh intervertebral discs to induce non-enzymatic glycation crosslinks over a period of sterile incubation.

Four-point lateral bending tests were conducted using an MTS 858 materials testing system with custom fixtures while load and displacement were recorded digitally. First the specimens were cleaned of muscle and other non-load supporting tissues, and then the terminal vertebrae were potted in polyurethane to half their height in square molds. The potted spine segments are then placed on the bottom 2 rollers such that the lateral sides of the spines were positioned in a vertical plane. The bending load was actuated by 2 upper rollers in contact with the central two vertebrae of the segment. Care was taken to ensure that the pre- and post-treatment positioning of the specimens on the rollers was similar. As an attribute of 4-point bending, the central region of the test specimen, including the central disc between the 2 upper rollers, has an evenly distributed shear load and bending moment. A ramp load to 100 N (0.5 mm/s) was applied in right and left lateral bending to each spine both prior to treatment and after crosslinking treatment.

The crosslinking reagents were delivered to each of the discs in each spine specimen by 2 to 3 injections into one lateral side of the spine. Each injection was comprised of 1 cc of reagent. A 26 gauge hypodermic needle was used. The treated segments were allowed to sit in a closed container wrapped in moist paper towels for 36 hours prior to final testing. After testing, the discs were cut transversely to visually document the region of the tissue contacted by the reagents.

Resistance to lateral bending and lateral bending stability were assessed by two measures, one elastic-plastic, the other viscoelastic. The first was the neutral zone (low-load) bending stiffness evidenced by the amount of deformation from 0.1 to 100 N of deforming force. The second was the hysteresis or bending energy lost or not stored by the tissues. Less hysteresis, or a lower percentage of hysteresis compared to strain energy or the amount of bending energy stored and returned, corresponds to greater capacity to bounce back from a bend rather than remain in the deformed position. It also reflects a more elastic, spring-like response as compared to a more viscous response.

The injections effectively distributed the crosslinking reagents to approximately one-half of the disc annulus, right or left half. See Table 3. The neutral zone bending stiffness was consistently increased by treatment only when the treated side was in tension. The average magnitude of stiffness increase was 12% with a 26% increase in the case of 0.66% genipin plus 0.1% proanthocyanidin treatment. The hysteresis was consistently decreased by treatment only when the treated side was in tension. The average decrease in hysteresis was 31% with a 37% decrease in the case of 0.66% genipin plus 0.1% proanthocyanidin treatment.

TABLE 3

| Specimen # Side Up | Treatment | Side Treated | Hysteresis | Max Displacement | Max Load | Loss of Hysteresis | Δ Stiffness: Compression side | Δ Stiffness: Tensionon side |
|---|---|---|---|---|---|---|---|---|
| 1L | Control | | 87.21 | 6.878 | 99.7 | | | |
| 1L | 0.50G | L | 97.47 | 8.381 | 99.0 | | −22% | |
| 1R | Control | | 170.73 | 8.860 | 98.7 | | | |
| 1R | 0.50G | L | 92.91 | 8.822 | 96.6 | 46% | | 0.43% |
| 2L | Control | | 64.41 | 3.463 | 99.3 | | | |
| 2L | 0.50G | L | 47.80 | 3.873 | 97.6 | | −12% | |
| 2R | Control | | 47.76 | 3.884 | 98.3 | | | |
| 2R | 0.50G | L | 40.28 | 3.573 | 101.1 | 16% | | 8% |
| 3L | Control | | 80.70 | 7.116 | 100.4 | | | |
| 3L | 0.33G | L | 58.79 | 5.041 | 99.7 | | 29% | |
| 3R | Control | | 78.52 | 5.951 | 100.0 | | | |
| 3R | 0.33G | L | 50.67 | 4.924 | 97.6 | 35% | | 17% |
| 4L | Control | | 61.97 | 5.62 | 101.1 | | | |
| 4L | 0.66G | | 49.88 | 5.259 | 99.3 | 20% | | 6% |
| 4R | Control | | 63.65 | 5.359 | 98.7 | | | |
| 4R | 0.66G | | 50.92 | 4.931 | 99.3 | | 8% | |
| 5L | Control | | 41.58 | 3.511 | 100.7 | | | |
| 5L | 0.66G + 0.1PA | | 49.87 | 4.049 | 101.4 | | −15% | |
| 5R | Control | | 74.89 | 4.683 | 100.4 | | | |
| 5R | 0.66G + 0.1PA | | 47.08 | 3.460 | 100.4 | 37% | | 26% |
| Average | | | | | | 31% | −2% | 12% |

These results demonstrate that crosslink augmentation with minimally non-toxic crosslinking reagents effectively reduces instability of intervertebral discs toward deforming forces as is expected in scoliotic spines. The stabilizing effect was observed to be greater with the 0.66% genipin plus 0.1% proanthocyanidin treatment. Consequently, by reducing the viscoelastic dissipation of bending energy and increasing the bounce-back of the discs (lowered hysteresis) and by increasing the bending stiffness in the direction that puts the treated side of the spine in tension, injectable non-toxic crosslink augmentation effectively resists scoliotic curve progression as well as other progressive spinal deformities.

Example 4

Tear Resistance

Ten annulus fibrosus circumferentially aligned specimens from bovine lumbar (T12-L5) intervertebral discs were divided into two groups and either soaked two days in a 0.15M PBS or a 0.15M PBS plus 0.33% genipin solution. A custom loading fixture attached to a uniaxial materials testing system was designed to hold an annulus specimen perpendicular to the travel of a metal cylinder placed in a pre-existing radial cut. The cylinder was then pulled radially (perpendicular to lamellae) towards the external layer. Time dependent force and displacement data was acquired simultaneously. Tearing resistance was quantified in two ways: peak force normalized by specimen thickness and tearing energy per area of tear. Differences between groups were analyzed using the Mann-Whitney non-parametric test.

Normalized peak force was 23.9 and 42.7 N/mm for control and genipin crosslinks groups respectively (p=0.076). Total energy per area of tear was 19.0 and 40.2 mJ/mm$^2$ for control and genipin groups (p=0.047).

Crosslink augmentation of the extracellular matrix of the annulus fibrosus was found to approximately double the peak force and the total energy required to propagate a radial tear. Injectable crosslink augmentation of the annulus fibrosus can prevent or slow down the degradation leading to loss of the contents of the disc's central region, whether it involves herniation of nucleus pulposus or expulsion of nucleus replacement devices or materials.

Example 5

Stability

While the overall success rate of lumbar discectomy is favorable, biomechanical investigation (Goel, 1985; 1986) and long-term clinical results (Kotilainen, 1993; 1994; 1998) suggest altered kinematic behavior and degenerative changes to the lumbar spine associated with significant loss of nucleus material and disc height, including the potential for lumbar instability. Currently, no treatments are available to aide in the prevention of instability and the subsequent degeneration following disc surgery. However, collagen crosslinking has shown favorable effects on disc tissue, including the ability to resist spinal deformity, and increase tensile strength and nutrient delivery. Therefore, the purpose of this experiment is to demonstrate that exogenous collagen crosslinking following posterior decompression surgery results in enhanced biomechanical properties of the intervertebral joint constituting a restabilization of the joint.

Fifteen fresh-frozen bovine lumbar functional spinal units were used for the experimental protocol utilizing a repeated measures design. An eight-axes materials testing device (EnduraTEC, Minnetonka, Minn.) was used to measure flexibility for each specimen in 3 conditions: intact, post-discectomy, and following collagen crosslinking injections. Following testing of the post-discectomy joints, specimens were separated into two groups based on crosslinker type. Discs were treated with either a non-enzymatic crosslinker (400 mM Methylglyoxal in 1×PBS, n=7) or an organic crosslinker (0.33% genipin in 1×PBS, n=8). The injection treatment consisted of injecting the post discectomy annulus fibrosus with less than 20 cc at 4 locations (directly anterior, directly posterior, and bilateral posterolateral,) using a 21-gauge needle, providing sufficient coverage of the disc. In order for the collagenous intervertebral disc to become adequately crosslinked, specimens remained at room temperature for a period of 48 hours, and were intermittently hydrated with % EDTA solution to prevent biological breakdown of tissue.

Continuous cycles of flexion/extension (sagittal plane) loads (±4 Nm) were applied and consequent motion characteristics were measured. The fourth loading cycle of each condition was used to assess instability. Instability was quantified by calculating Neutral Zone (NZ), % Hysteresis (HYS), Range of Motion (ROM), and % Strain Energy (SE, SE=100-HYS). Variables were normalized with respect to intact values. Pairwise comparisons were made using the Wilcoxon Signed-Rank test (significance level, p<0.05).

Discectomy induced significant changes in NZ (p=0.009), HYS (p=0.004), ROM (p=0.003), and SE (p=0.004) when compared to intact, demonstrating the destabilizing effect of partial disc removal. All specimens, regardless of crosslinking reagent, showed decreased instability following injection treatment for all variables (all p-values≦0.018). No significant differences existed between intact and post-injection conditions for either group.

Exogenous collagen crosslinking of the intervertebral disc following a common surgical procedure is effective in restabilizing the intervertebral joint in all measured parameters. In fact, under the applied loads used in this study, nonenzymatic (methylglyoxal) and organic (genipin) crosslinking essentially returned each segment to the intact state (most within 6%, NZ within 18%). Implementing exogenous collagen crosslinking as an adjunct to current clinical procedures may be beneficial in preventing or delaying subsequent spinal instability and degenerative change associated with spinal decompression surgery.

One can treat a patient who has undergone posterior decompression surgery including bilateral laminectomies and discectomy by treating the remaining intervertebral disc (annulus fibrosus) at the affected level with a crosslinking agent, such as 400 mM L-Threose in saline (0.15M) or a solution comprised of 200 mM methylglyoxal in saline or a solution of 200 mM glyoxal or a solution 200 mM EDC or a solution comprised of 50-100 µg lysyl oxidase in a 0.1 M urea saline solution or a solution comprised of 50 µg/ml human recombinant transglutaminase in saline, or a solution comprised of 200 µg/ml of purified animal liver transglutaminase in saline. Immediately after the posterior decompression surgery including discectomy or within a few days after surgery the crosslinking agent can be injected into the whole remaining disc at the surgically decompressed levels. According to the preference of the physician administering the treatment, multiple injections of a preferred, non-toxic crosslinking agent can be performed through a single or multiple injection sites. Fluoroscopic or other imaging means can be used to deliver the crosslinking agent to the selected tissues. The patient should be instructed to avoid strenuous activities for a period of a few days.

The invention has been described in terms of certain preferred and alternate embodiments which are representative of only some of the various ways in which the basic concepts of the invention may be implemented. Certain modification or variations on the implementation of the inventive concepts which may occur to those of ordinary skill in the art are within the scope of the invention and equivalents, as defined by the accompanying claims.

Example 6

Hydraulic Permeability

By measuring the change in hydration of different regions of the intervertebral disc (nucleus pulposus, inner annulus, and outer annulus fibrosus) prior to and after periods of soaking, sustained compressive loading, and resoaking, the fluid flux to and from different regions can be determined. By comparing these measurements between control discs and discs treated with crosslinking reagents known to have minimal cytotoxicity, we see the effect of crosslinking treatment on fluid flux and permeability.

A total of 24 calf (4 month-old bovine) intervertebral discs were used for this study. Water content of three different areas of the discal tissue were tested—the nucleus pulposus, inner annulus fibrosus and outer annulus fibrosus. Hydration change was determined by weighing the specimen using a micro-balance (sensitivity: 0.1 mg). Water content (M) was calculated as:

$$M = (\text{Wet Weight} - \text{Dry Weight})/\text{Wet Weight} = g\ H_2O/g\ \text{Wet Weight}$$

The drying procedure consisted of putting the specimens in the oven with a controlled temperature of 90° C. for 24 hrs. The specimens were separated into four tests:

1. Group A: Three specimens were in this group. It served as a control group. The specimens were soaked in PBS (phosphate buffered saline) for 1 day and then the hydration analysis was performed.

2. Group B1: Four specimens were in this group. In addition to the one day PBS soaking, the specimens soaked in PBS for 2 more days as a control and then the hydration analysis was performed.

Group B2: Five specimens were in this group. In addition to the one day PBS soaking, the specimens were soaked in 0.33% genipin solution for 2 days and then the hydration analysis was performed.

3. In group C, a small daytime amount of constant compressive loading (creep) was simulated.

C1: Three specimens were in this group. The specimens were soaked in PBS for 3 days and then 750N of compression was applied by a materials testing machine for 1 hour. The disc was compressed in a 5 degree of flexion posture produced by two rollers attached to the loading ram of the materials testing machine. The hydration analysis was performed immediately after the creep loading.

C2: Three specimens were in this group. The specimens were soaked in 0.33% Genipin solution for 2 days after 1 day of PBS soaking and performed identical creep loading with 750N compressive load. The hydration analysis was performed immediately after the creep loading.

4. In group D, the imbibition of water following a period of compressive loading that typically occurs in the night time as a person is in a recumbent posture was simulated.

D1: The specimens were soaked in PBS solution for 3 days and then 1 hr of creep loading at 750N was applied. After the creep loading, the specimens were placed in a container in 1 PBS for one more day followed by the hydration analysis.

D2: Three specimens were included and were soaked in 0.33% genipin solution for 2 days after one day of PBS soaking. A creep load of 750N for 1 hr was then applied. The specimens were put in PBS for another day followed by hydration analysis.

As shown in Table 4, in general, creep loading expels fluid out of the tissues and after creep re-absorption of fluid occurs. The result pertinent to the present invention was that there was a combined 64% increased fluid flow into and out of the central nucleus region in the genipin crosslinking reagent treated discs compared to controls.

TABLE 4

|  | Gr B1 | Gr B2 | Gr C1 | Gr C2 | Gr D1 | Gr D2 | Control Flux | Genipin Flux | % increase by Genipin |
|---|---|---|---|---|---|---|---|---|---|
| Inner AF | 0.768771 | 0.762891 | 0.745779 | 0.739397 | 0.808709 | 0.816669 | 0.08592 | 0.10077 | 17.3% |
| Outer AF | 0.723259 | 0.726776 | 0.696626 | 0.692404 | 0.720096 | 0.710972 | 0.050010 | 0.05294 | 5.7% |
| NP | 0.834041 | 0.831405 | 0.825998 | 0.816964 | 0.848403 | 0.852357 | 0.03045 | 0.04983 | 63.7% |

These results demonstrate that augmentation of crosslinking of intervertebral disc tissue resulted in an increased fluid flow into and out of the central region of the intervertebral disc. This increased fluid flux to the disc nucleus indicates that this treatment effects an increase of nutrients supplied to cells in the central region of the disc as well as an increased removal of cell and matrix waste products.

Example 7

Concentration and pH Optimization

In order to determine the effective concentration range for various crosslinking reagents we incubated samples of annulus tissue in increasing concentrations of either genipin (GP), methylglyoxal (MG), proanthrocyanidin (PA), L-threose (LT), D-threose (DT), dimethylaminopropyl) carbodiimide hydrochloride (EDC) or transglutaminase (TG). Crosslinking efficiency was measured indirectly by monitoring the release of peptides containing hydroxyproline upon subsequent digestion with collagenase. Glutaraldehyde (GA), a commonly used, but highly toxic protein crosslinker was used as a positive control. Each experiment was conducted twice (with the exception of GA) and the data are summarized in FIG. 1. In most cases plateaus were reached at a point where crosslinking was essentially complete. For example, MG crosslinking appeared to be complete at 50 mM, suggesting that at this point the crosslinker was saturating and the rate of the reaction could not be accelerated by the further addition of more reagent. In the cases of LT, DT and TGe, the length of crosslinking time of the incubations were insufficient to result in complete protection of the collagen from the protease under these digestion conditions. For DT and LT a plateau was reached at approximately 50 mM, beyond which no further crosslinking was observed, suggesting that the reaction could not proceed any faster beyond this concentration. TG did not reach a plateau even at the highest concentration tested. (2 U/ml), although it did appear to be approaching such a point. Higher concentrations were not tested due to the high cost of this reagent.

One of the critical parameters that governs the efficacy of a crosslinking agent is pH. Thus selection of the pH is an important consideration in the process of formulation development. Furthermore, if the optimal pH of the crosslinker is very different from that of the tissue being treated, incorporation of a buffer strong enough to maintain the optimal crosslinking pH is also critical. For example, the pH environment of spinal discs, particularly of those in the process of DDD, is in the acidic range due to the avascular nature of the tissue which therefore must generate much of its energy from anaerobic glycolysis and the concomitant formation of lactic acid (1). If crosslinking of disc tissue is accelerated by alkaline pH, it would be beneficial to buffer the delivery vehicle sufficiently to raise the pH in vivo at least temporarily.

One of the main targets of the inventor's crosslinking agents on proteins is the amino acid lysine (and to some extent also argenine). In order for this residue to be reactive, it needs to be present in its uncharged form so that it can act as an electron donor to the crosslinker. Since the $pK_a$ of $\epsilon$-amine of lysine in a protein varies approximately from 9 to 10 (Zhang and Vogel, 1993), it seemed likely that crosslinking would be favored by alkaline pH. Both MG and GP, for example, act primarily by reaction with amines (Chellan and Nagaraj, 1999; Sung et al., 2003)).

Figure 2:
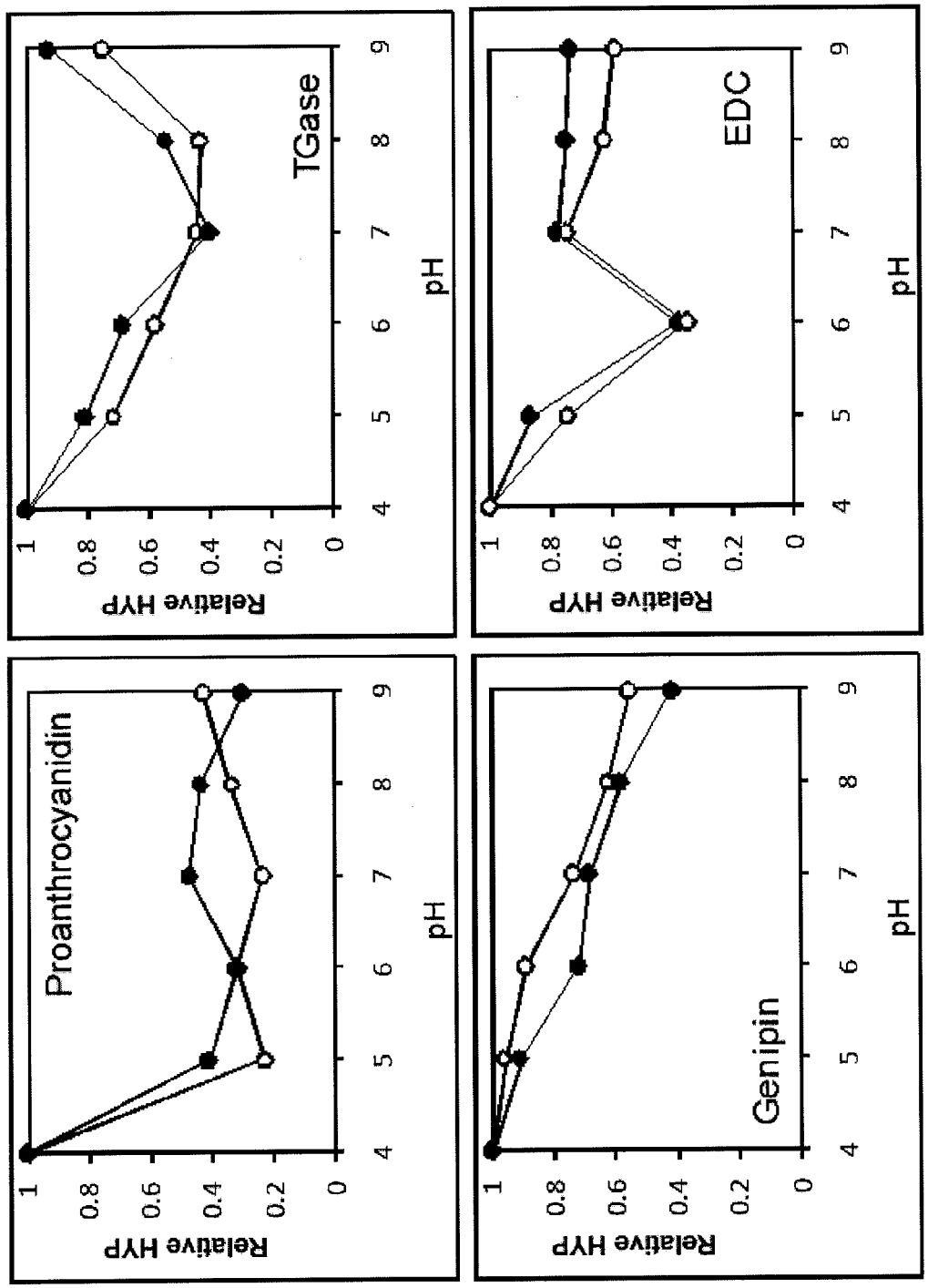
FIG. 2—pH dependence of protein crosslinking reagents. Homogenized annulus tissue was treated with sub-saturating concentrations of various crosslinkers at varying pH and incubated for either 1 hr (EDC, GP, MG, PA and GA), 2 hrs (TG) or 6 hrs (LT). Crosslinking was quantified by determining the amount of hydroxyproline (HYP) released from the tissue by collagenase digestion.
Figure 2:
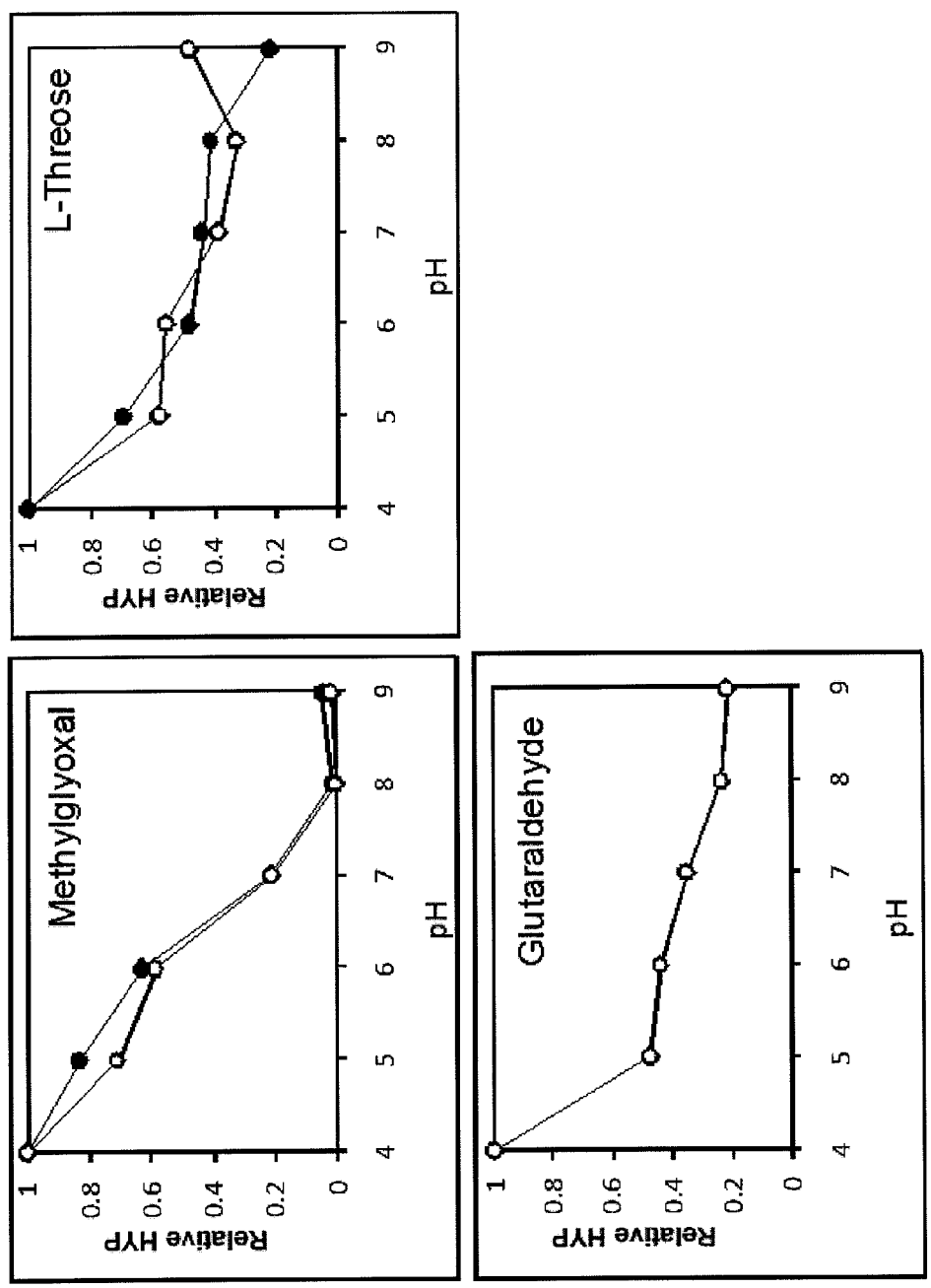

To test this hypothesis, the inventors subjected calf annulus fibrosus tissue to crosslinking with sub-saturating levels of our reagents at varying pH. In order to maintain optimal buffering capacity at each pH, different buffers were selected for each point. The buffers chosen (based on their $pK_a$s) were: sodium acetate (pH 4), sodium cacodylate (pH 5), MES (pH 6), MOPS (pH 7), EPPS (pH 8) and sodium borate (pH 9). These experiments showed that MG, LT and GP all function better in disc tissue at the higher pH levels, with MG being particularly sensitive to the alkalinity of the solution (FIG. 2). EDC and TG both required a relatively narrow pH range, as previously reported (Zhang et al., 2004; Chung et al., 1970), while PA appeared relatively insensitive to pH.

The enhanced activity of MG under alkaline conditions has been reported previously (Murata-Kamiya and Kamiya, 2001). In the inventor's disc annulus testing, MG activity appeared equally efficient at pH 8 and 9, however, this may have been due to over-saturation with this reagent. At lower MG concentrations it is feasible that MG would be more effective at pH 9 than 8. However, in order to produce a product that is closer to physiological pH (i.e., 7), the inventors selected pH 8 for further optimization. It should be noted, however, that a putative product would most likely be more efficacious at pH 9 which might outweigh potential concerns regarding its high alkalinity. In addition, due to the acidic nature of the disc, a pH 9 buffer might offer an additional advantage by potentially allowing the use of a lower buffer concentration to maintain an alkaline pH. This might be of utility if a high concentration of pH 8 buffer produced adverse effects due to its hypertonicity.

Figure 3:
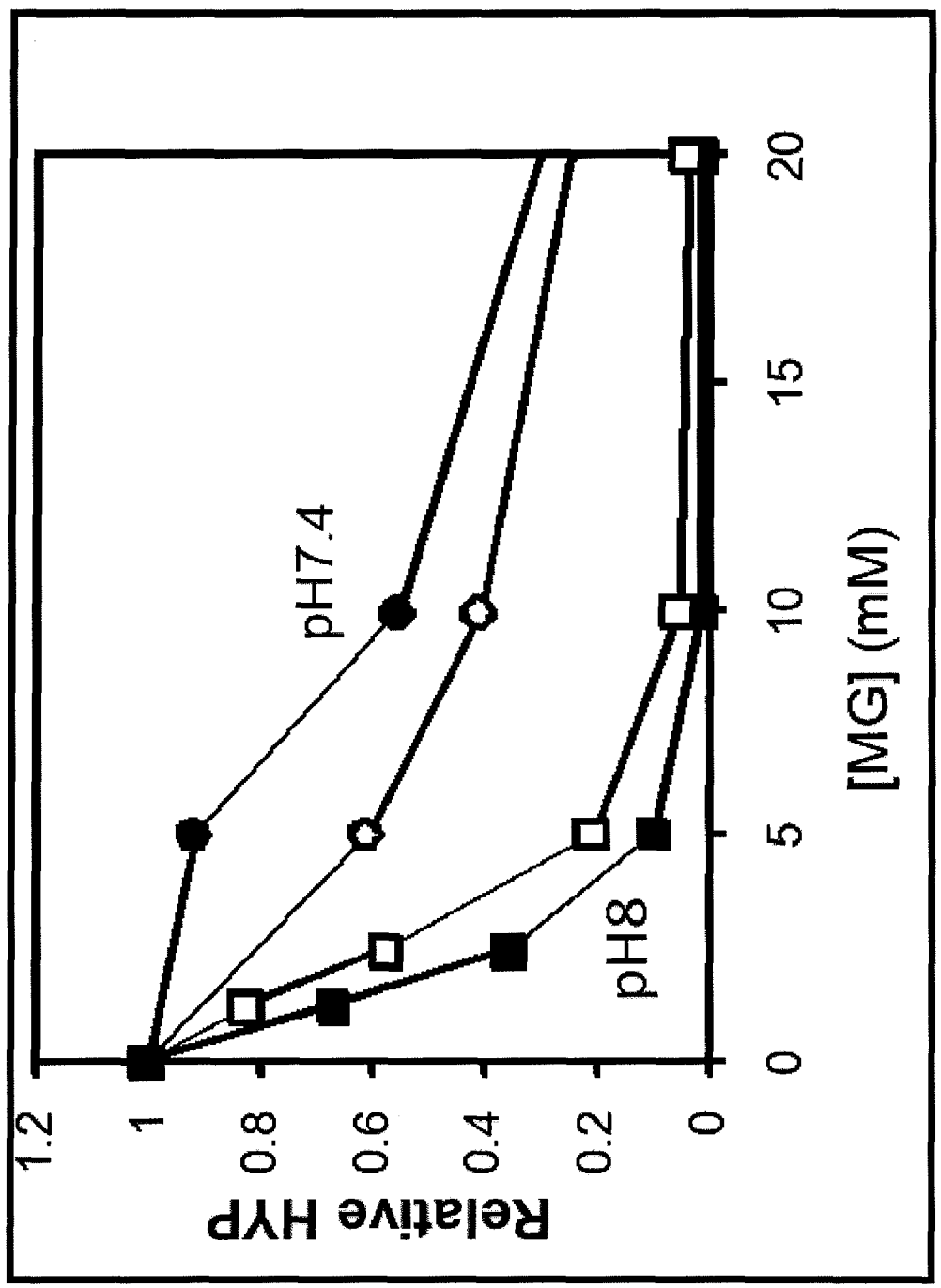
FIG. 3—Effect of pH on MG crosslinking activity. Samples of annulus were treated with increasing concentrations of MG in either PBS (pH 7.4) or in 100 mM EPPS buffer, pH8. Crosslinking was quantified by determining the amount of hydroxyproline (HYP) released from the tissue by collagenase digestion.

The fact that MG crosslinking was complete at both pH 8 and 9 under these conditions (see FIG. 2), prompted us to re-titrate this reagent at an elevated pH, i.e., pH 8. MG displayed a marked increase in its crosslinking ability at pH 8 compared to pH 7 (FIG. 3). Under these conditions the MG was saturating at a concentration of 10 mM.

Example 8

Effect of Buffers

The inventors chose EPPS as the pH 8 buffer in the above pH studies because of concerns with reaction of the crosslinkers with the amine in the more commonly used buffer, Tris. However, since Tris is currently used clinically for the treatment of blood acidosis, the inventors next sought to determine whether it could be substituted for EPPS in a prototype formulation without affecting the reactivity of the crosslinking reagent.

Figure 4A:
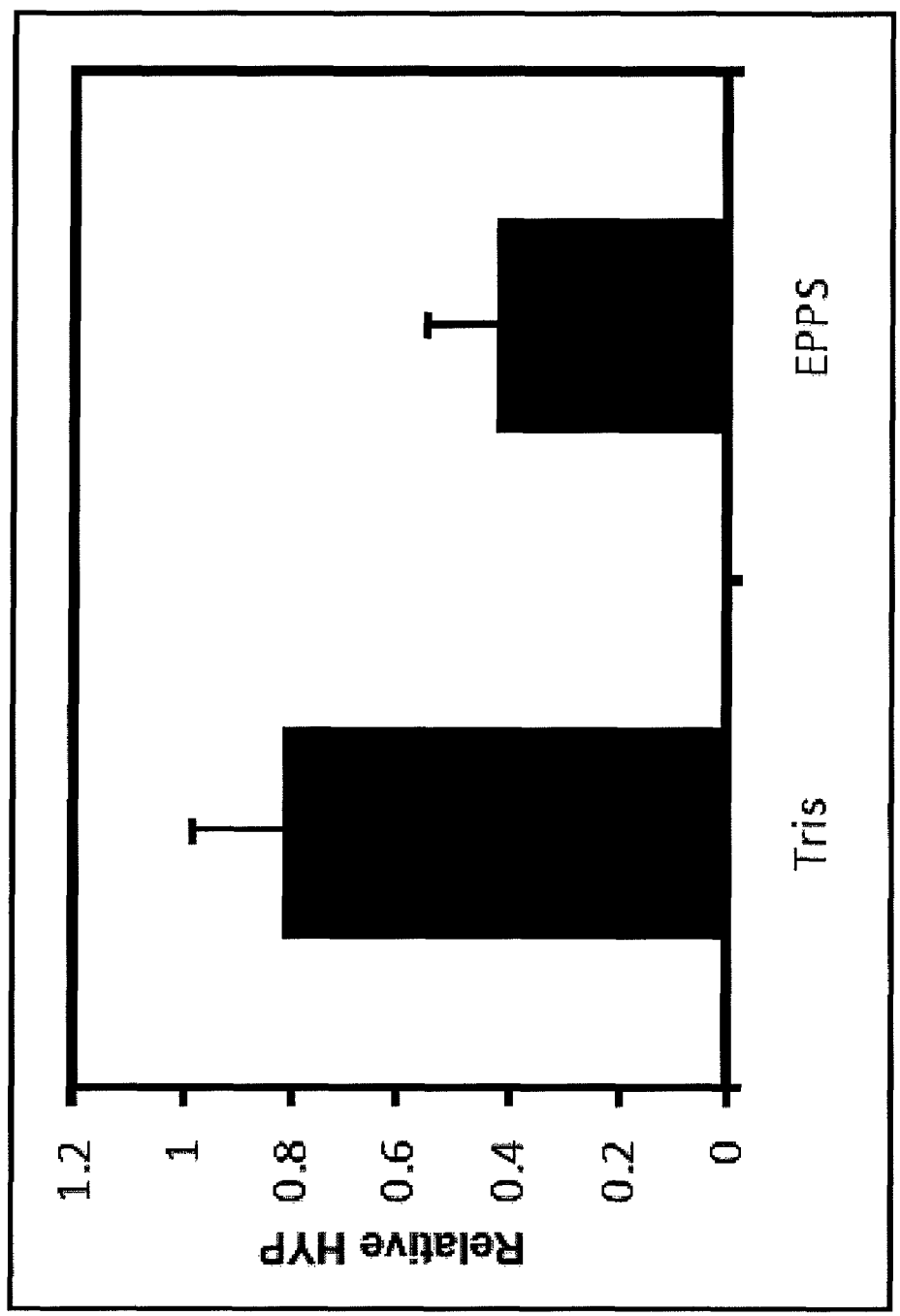
FIGS. 4A-B—Effect of buffer on methylglyoxal-mediated crosslinking. A subsaturating concentration of MG was used to treat annulus tissue at pH 8.0 in either EPPS or Tris buffer (FIG. 4A). Alternatively, annulus tissue was treated with various concentrations of GP in either Tris or EPPS buffer at pH 9.0 (FIG. 4B). The relative extent of crosslinking was determined indirectly by measuring the release of hydroxyproline from the tissue upon proteolysis with collagenase. Data are presented as the optical density (OD) obtained relative to untreated tissue controls. Data in FIG. 4A are presented±SD. n=10.
Figure 4B:
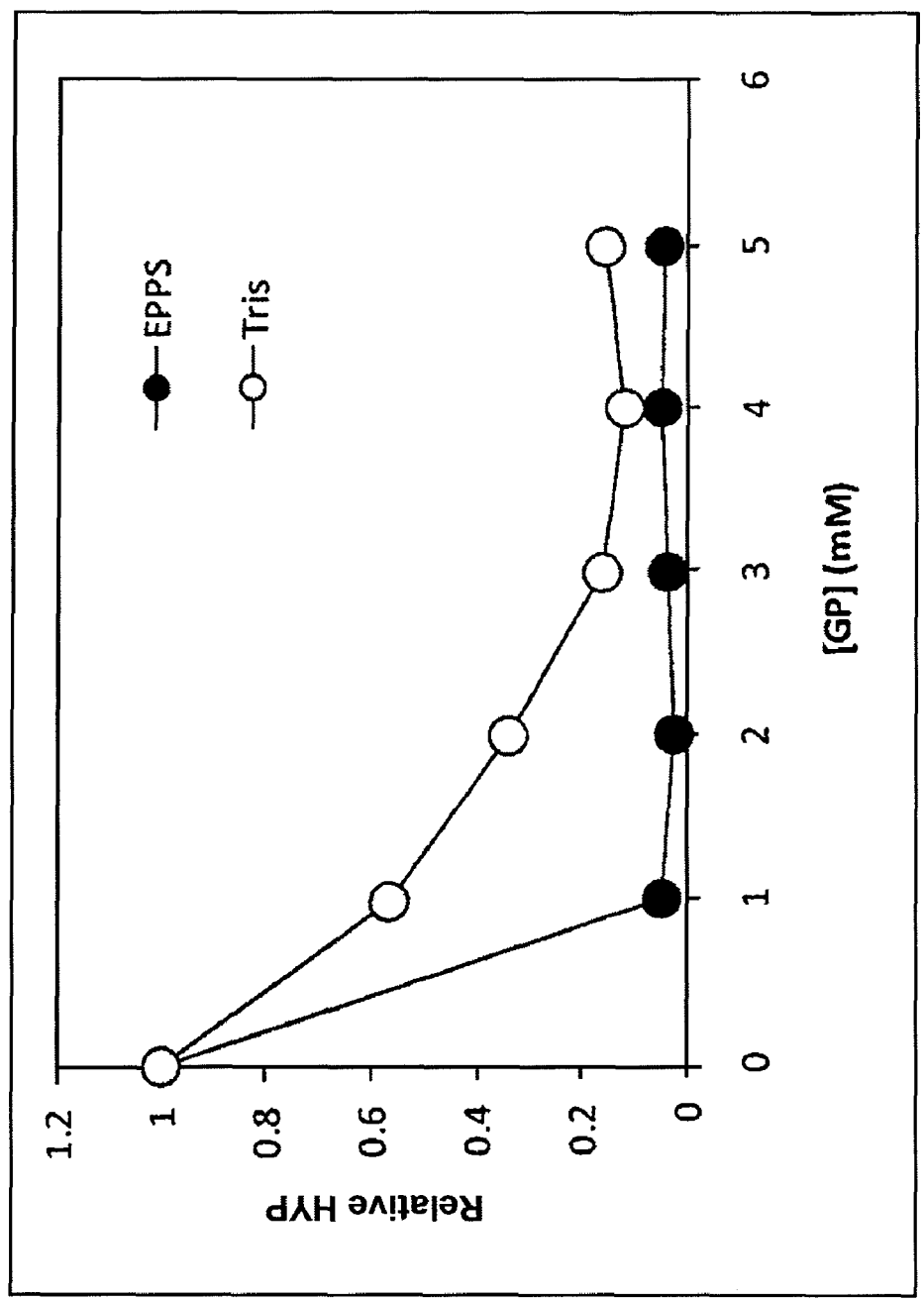

Tissue was treated with sub-saturating concentrations of MG at pH 8 using either 100 mM EPPS or Tris as the buffering species. MG was indeed less effective in the presence of Tris buffer, possibly due to reaction with the primary amine in this molecule (FIG. 4A), exhibiting almost 2-fold more activity in EPPS when compared to Tris under these conditions ($p<0.0001$, $n=10$). In a separate experiment, tissue was treated with varying concentrations of GP in either 100 mM EPPS or 100 mM Tris buffer at pH 9. As for MG, GP was more effective in EPPS buffer than in Tris (FIG. 4B). These data suggest that EPPS would be a good choice of buffer for clinical use of both GP and MG in disc tissue. The inventors is currently unaware of any prior art describing these buffer effects in the literature.

Example 9

Enhancers of MG Crosslinking

Figure 5:
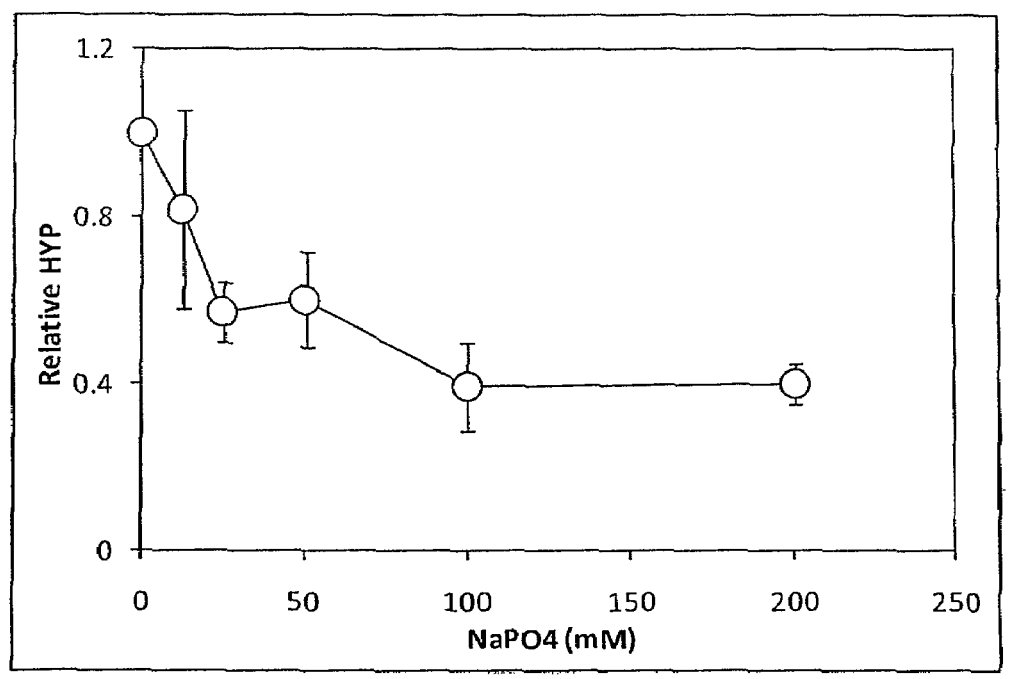
FIG. 5—Effect of sodium phosphate on methylglvoxal-mediated crosslinking. Sub-saturating concentrations of MG were used to treat annulus tissue in Tris buffer at pH 8.0 containing increasing concentrations of sodium phosphate. The relative extent of crosslinking was determined indirectly by measuring the release of hydroxyproline from the tissue upon proteolysis with collagenase. Data are presented as the optical density (OD) obtained relative to untreated tissue controls±SD. n=4.
Figure 6:
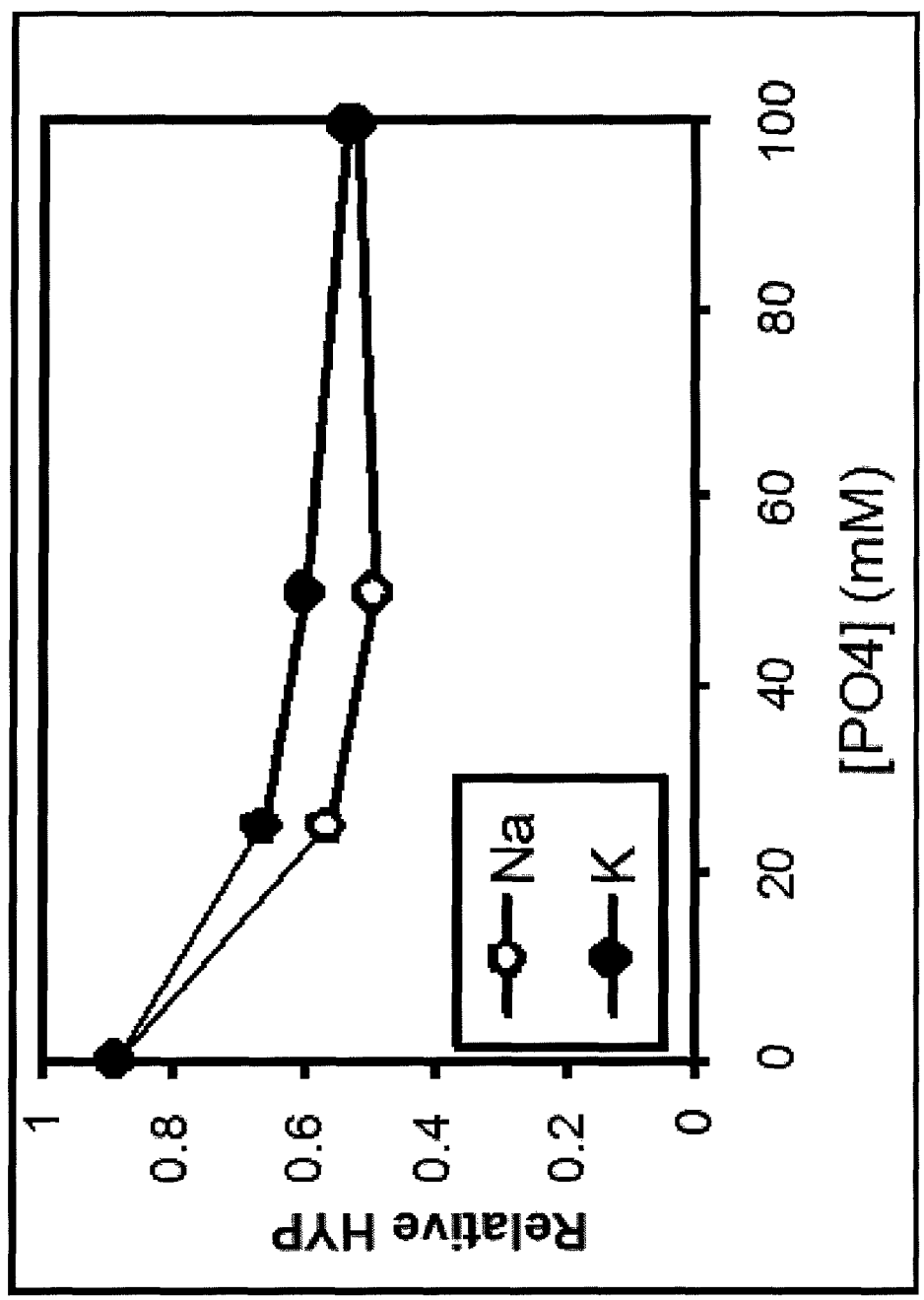
FIG. 6—Effect of sodium and potassium phosphate on methylglyoxal-mediated crosslinking. Sub-saturating concentrations of MG were used to treat annulus tissue in Tris buffer at pH 8.0 containing increasing concentrations of either sodium or potassium phosphate. The relative extent of crosslinking was determined indirectly by measuring the release of hydroxyproline from the tissue upon proteolysis with collagenase. Data are presented as the optical density (OD) obtained relative to untreated tissue controls.

It has been previously reported that phosphate ions are capable of enhancing the protein reactivity of glucose, possibly by acting as a proton-transferring catalyst (Watkins et al., 1987; Fu et al., 1992). Since MG shares a similar reaction mechanism to proteins with glucose, the inventors speculated that phosphate ions may also enhance MG-mediated protein crosslinking. He therefore sought to examine the effects of added phosphate on the crosslinking rate of MG at pH 8 with intervertebral disc tissue. Firstly disc annulus tissue was treated with sub-saturating concentrations of MG in the presence of 100 mM Tris buffer at pH 8 and increasing concentrations of sodium phosphate. Under these conditions sodium phosphate concentrations did indeed appear to enhance disc tissue crosslinking in a dose-dependent manner (FIG. 5). This must have been an effect of phosphate, and not sodium, since potassium phosphate exhibited a very similar effect (FIG. 6).

In the above experiments, the inventors showed that phosphate does indeed appear to enhance MG-mediated crosslinking in disc tissue, even in the presence of Tris buffer, which the inventors have shown to be inhibitory relative to EPPS buffer. Furthermore, in the study by Watkins et al. (1987), the phosphate itself was used as the buffering species and so the experiments were conducted pH 7.4, which the inventors have already shown is below the optimal for the crosslinking reaction, since phosphate does not function effectively as a buffer at pH 8 or 9.

Figure 7:
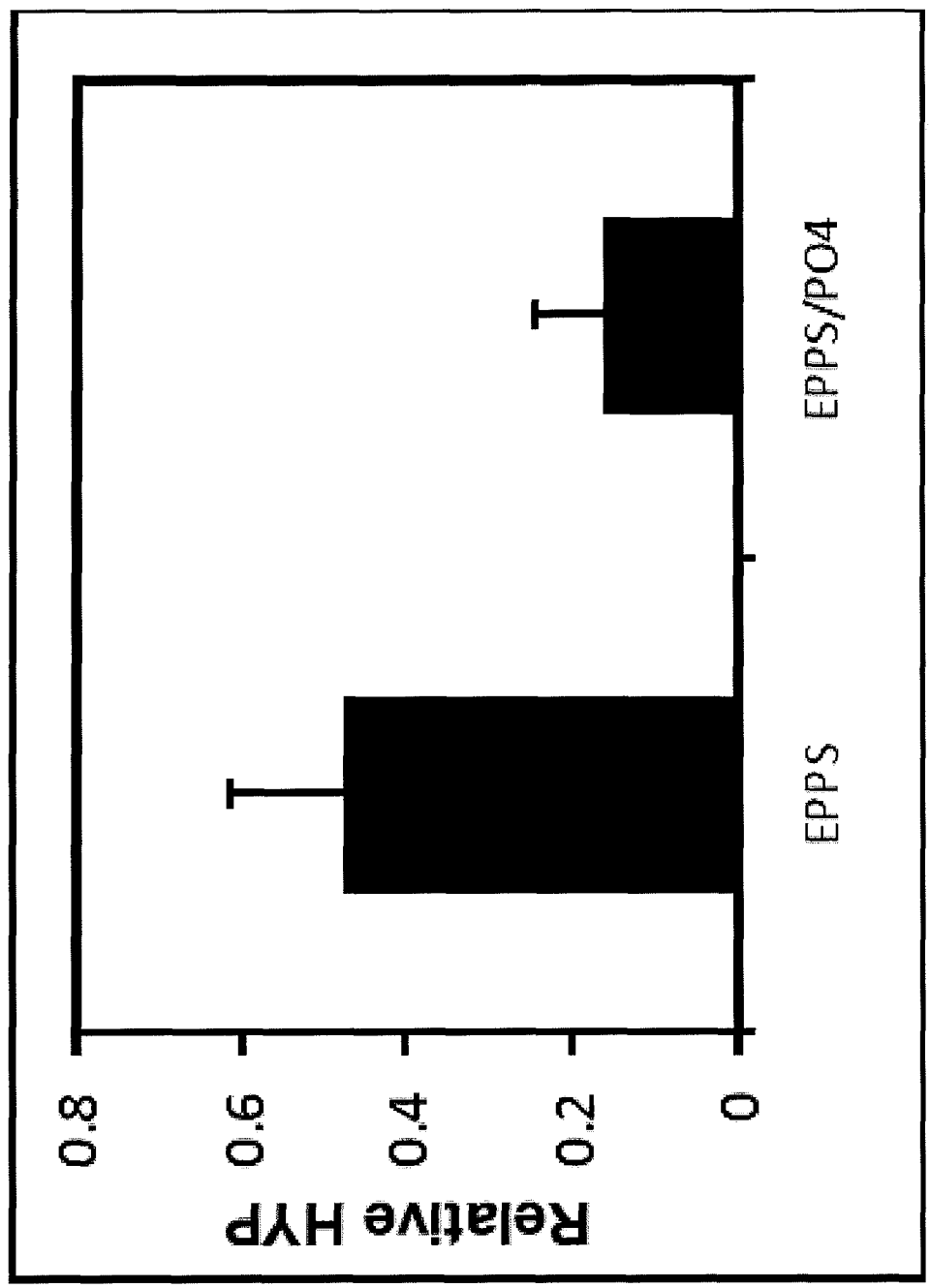
FIG. 7—Effect of potassium phosphate on methylglyoxal-mediated crosslinking in EPPS buffer. Sub-saturating concentrations of MG were used to treat annulus tissue in EPPS buffer at pH 8.0 containing 100 mM potassium phosphate. The relative extent of crosslinking was determined indirectly by measuring the release of hydroxyproline from the tissue upon proteolysis with collagenase. Data are presented as the optical density (OD) obtained relative to untreated tissue controls±SD. n=6.

The inventors next decided to determine whether phosphate ions could further enhance the reactivity of MG in EPPS buffer with disc tissue. The inventors incubated tissue in 100 mM EPPS buffer at pH 8 and in the presence or absence of 100 mM potassium phosphate. The pH of the buffer was re-adjusted to 8.0 after addition of the phosphate and, under these conditions, the EPPS would be acting as the predominant buffering species. This showed that phosphate did indeed enhance MG crosslinking approximately 3-fold, even in EPPS buffer at pH 8 (FIG. 7). A t-test showed that these results were marginally significant ($p=0.1$).

Figure 8:
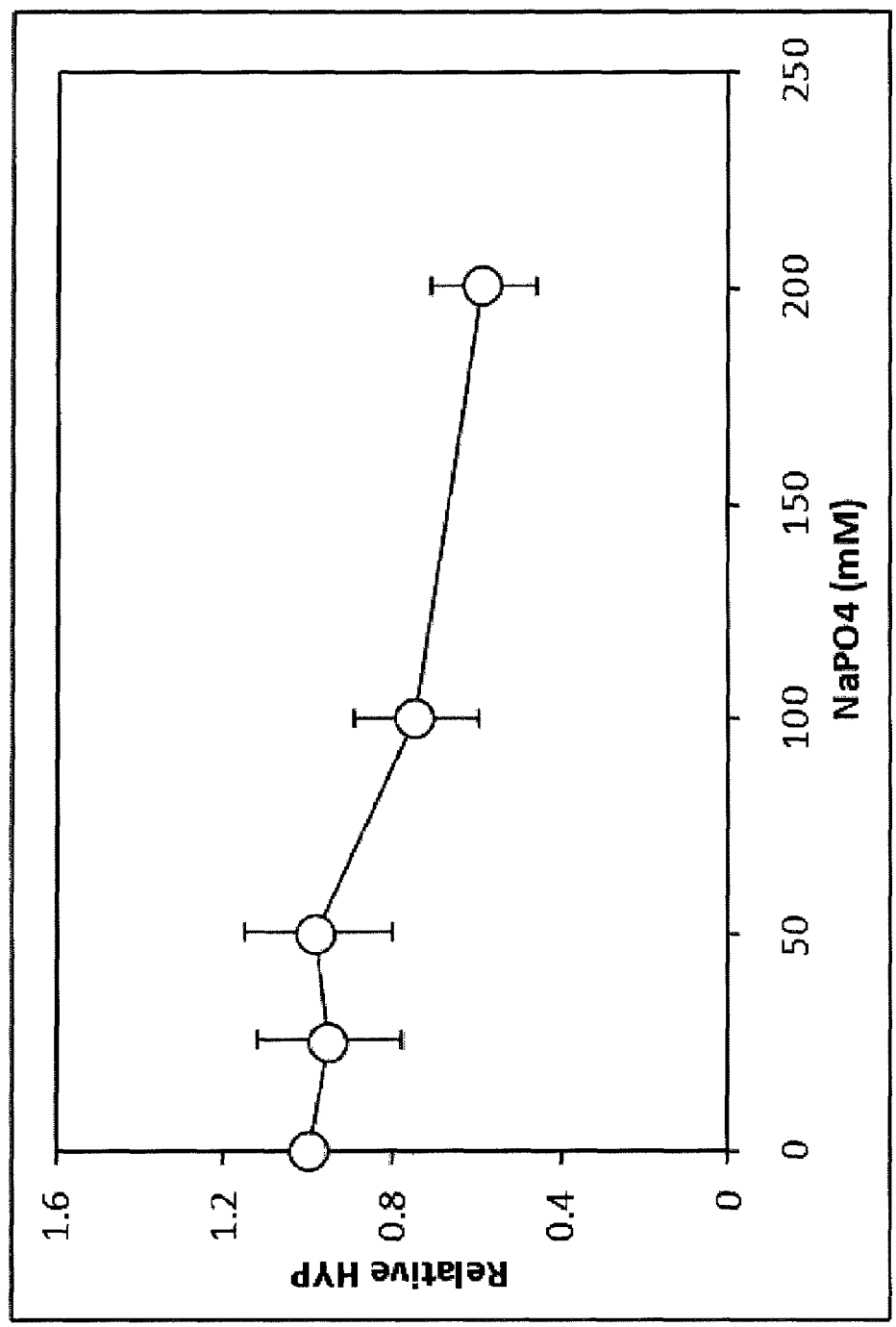
FIG. 8—Effect of sodium phosphate on genipin-mediated crosslinking. Sub-saturating concentrations of GP were used to treat annulus tissue in Tris buffer at pH 8.0 containing increasing concentrations of sodium phosphate. The relative extent of crosslinking was determined indirectly by measuring the release of hydroxyproline from the tissue upon proteolysis with collagenase. Data are presented as the optical density (OD) obtained relative to untreated tissue controls±SD. n=3.

Since phosphate ions enhance MG-mediated crosslinking, the inventors sought to determine whether this was the case with other crosslinking agents. While phosphate did not have any substantial proanthrocyanidin-mediated crosslinking affect (data not shown), genipin did display a dose-dependent enhancement (FIG. 8). This result was surprising since GP reacts with proteins via a very different chemistry to MG. The inventors are currently unaware of any reports in the literature describing this effect.

An additional advantage to incorporating phosphate into a Tris or EPPS buffer at pH 8 or 9 is that the phosphate will enhance the effective buffering range of the vehicle. While both Tris and EPPS rapidly lose their buffering capacity at neutral pH, the phosphate will then become effective. While both GP and MG are not as effective at pH 7, they are still active. Thus the inclusion of phosphate would prolong the exposure of the crosslinking agents to the tissue under conditions where crosslinking can occur. This might be particularly important in the acid environment encountered in a disc undergoing DDD.

Figure 9:
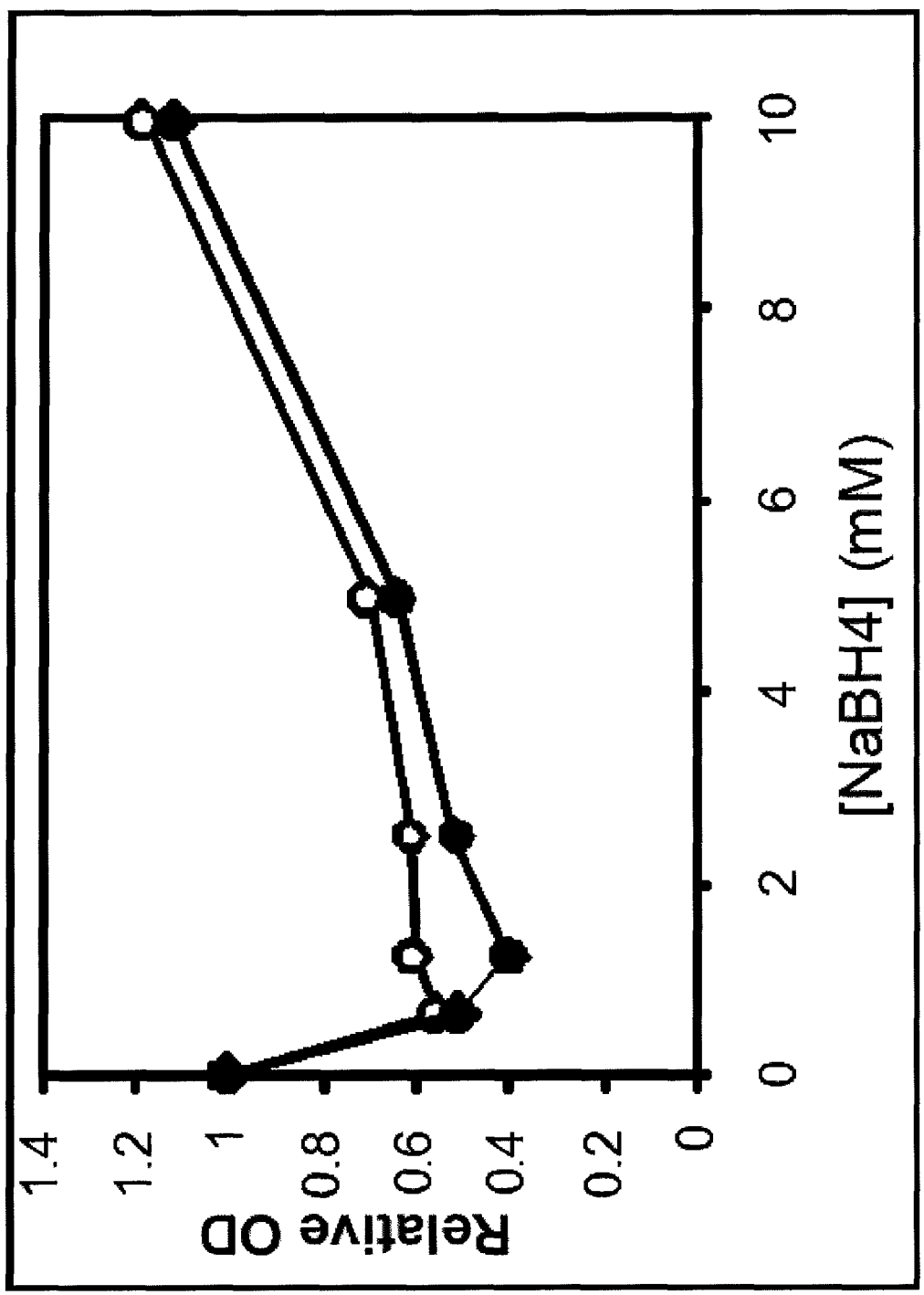
FIG. 9—Effect of sodium borohydride on methylglyoxal-mediated crosslinking. Sub-saturating concentrations of MG were used to treat annulus tissue in MOPS buffer at pH 7.0 containing increasing concentrations of sodium borohydride. The relative extent of crosslinking was determined indirectly by measuring the release of hydroxyproline from the tissue upon proteolysis with collagenase. Data are presented as the optical density (OD) obtained relative to untreated tissue controls and show the results of two separate experiments.
Figure 10:
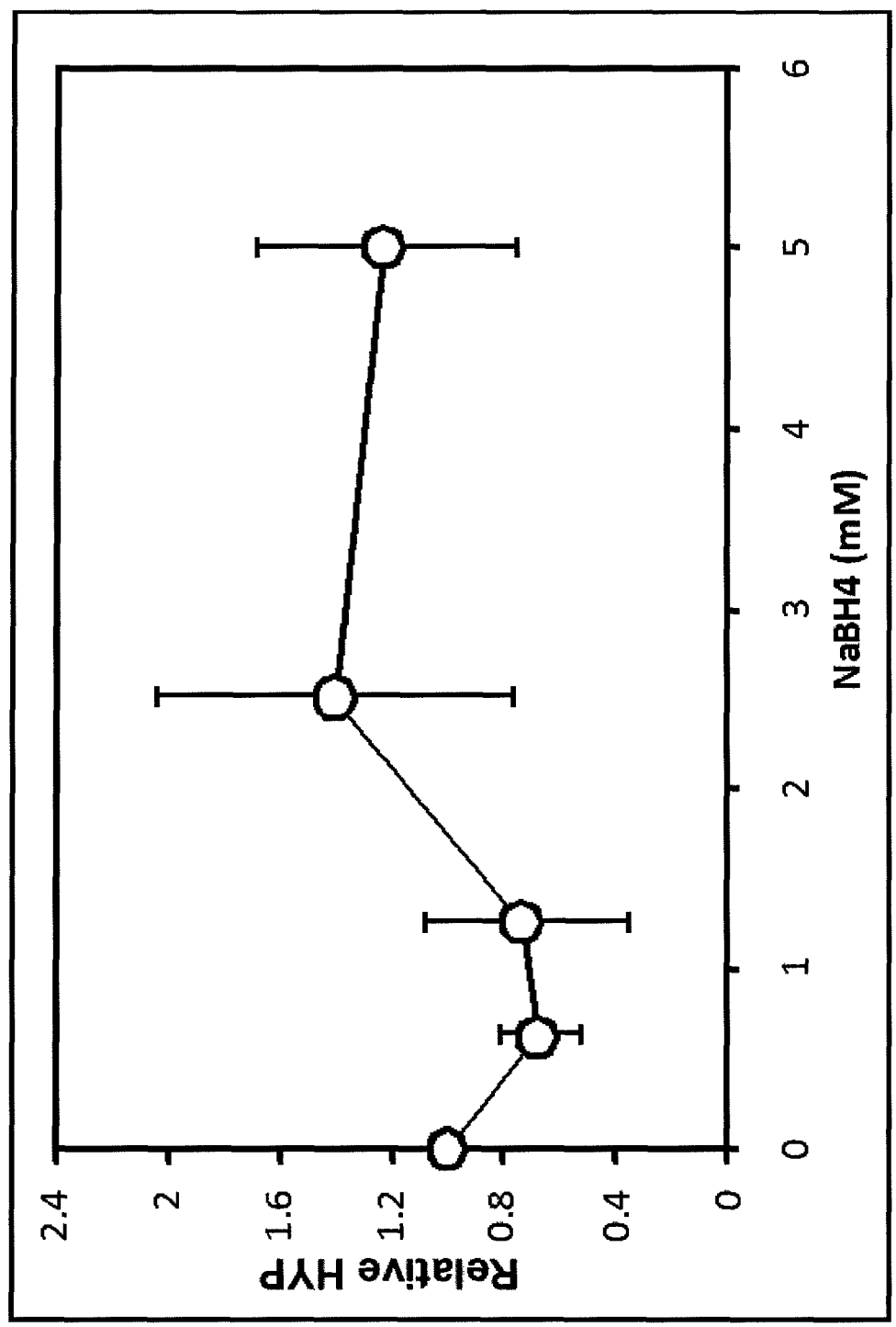
FIG. 10—Effect of sodium borohydride on methylglyoxal-mediated crosslinking in EPPS Buffer. Sub-saturating concentrations of MG were used to treat annulus tissue in EPPS buffer at pH 8.0 containing increasing concentrations of sodium borohydride. The relative extent of crosslinking was determined indirectly by measuring the release of hydroxyproline from the tissue upon proteolysis with collagenase. Data are presented as the optical density (OD) obtained relative to untreated tissue controls and show the results of four separate experiments±S.D.

It has also been previously reported that sodium borohydride can also enhance MG-mediated crosslinking by the reduction of a reversible Schiff's base intermediate formed during the crosslinking reaction (Murata-Kamiya and Kamiya, 2001). The inventors tested this in his system by incubating intervertebral disc tissue in sub-saturating concentrations of MG in 100 mM MOPS at pH 7 and increasing concentrations of sodium borohydride. This showed that at borohydride concentration of 1-5 mM the crosslinking reaction in disc tissue was indeed enhanced (FIG. 9). At 10 mM borohydride, however, the reagent appeared to be inhibitory as the tissue appeared to be more susceptible to digestion than in its absence. The effective range for borohydride was narrower in a buffer that was more optimal for MG-mediated crosslinking (i.e., EPPS buffer at pH 8.0), with enhancement only being observed below 1.5 mM (FIG. 10).

Murata-Kamiya and Kamiya (2001) have disclosed that borohydride will favor reaction of methylglyoxal with proteins: "Methylglyoxal is known to form reversible imine intermediates (Schiff base) in reactions with proteins under physiological conditions. Reduction of the imine bond by $NaBH_4$ leads to the formation of irreversibly bound complexes between the protein and methylglyoxal." They did not, however, disclose that this is the case from its crosslinking action nor that higher concentrations of borohydride may be detrimental to the crosslinking reaction in disc tissues.

Example 10

Effect of Surfactants on Crosslinker Diffusion

During clinical application of NEXT, the crosslinking reagent will be injected into the spinal disc. In order to ensure design of an optimal delivery system and procedure, knowledge of the diffusion rate of the reagent is crucial. The inventors decided to address this issue by conducting a diffusion study using colored reagents. The candidate crosslinking reagents can be divided into two classes based on molecular weight, i.e., small and large. In order to assess their potential diffusion rates, the inventors selected two molecules for this study. For smaller molecules, genipin (GP) was chosen because tissue crosslinked by this reagent is stained blue following exposure to air, thereby allowing the diffusion zones to be easily observed. While it could be argued that GP is not a true marker of bona fide small molecule diffusion and may underestimate the true diffusion rate (because it reacts with, and is immobilized by, the tissue through which it is moving), the inventors felt it was a more relevant test molecule since its reaction with the tissue would provide a more accurate estimation of the diffusion of small molecular weight crosslinkers within the disc. As a marker for a large molecular weight crosslinker (i.e., an enzymatic crosslinker such as transglutaminase (TG) or lysl oxidase (LO)), which could not be visualized directly as was the case for GP, the inventors chose bovine serum albumin (BSA) conjugated to the fluorophore Texas Red (TR). BSA was considered an appropriate marker for the enzymatic crosslinkers because its molecular weight of 66 kD compares to the 85 kD for TG and the 28 kD for LO, while the color of the TR facilitates the visualization of the molecule following injection.

Figure 11:
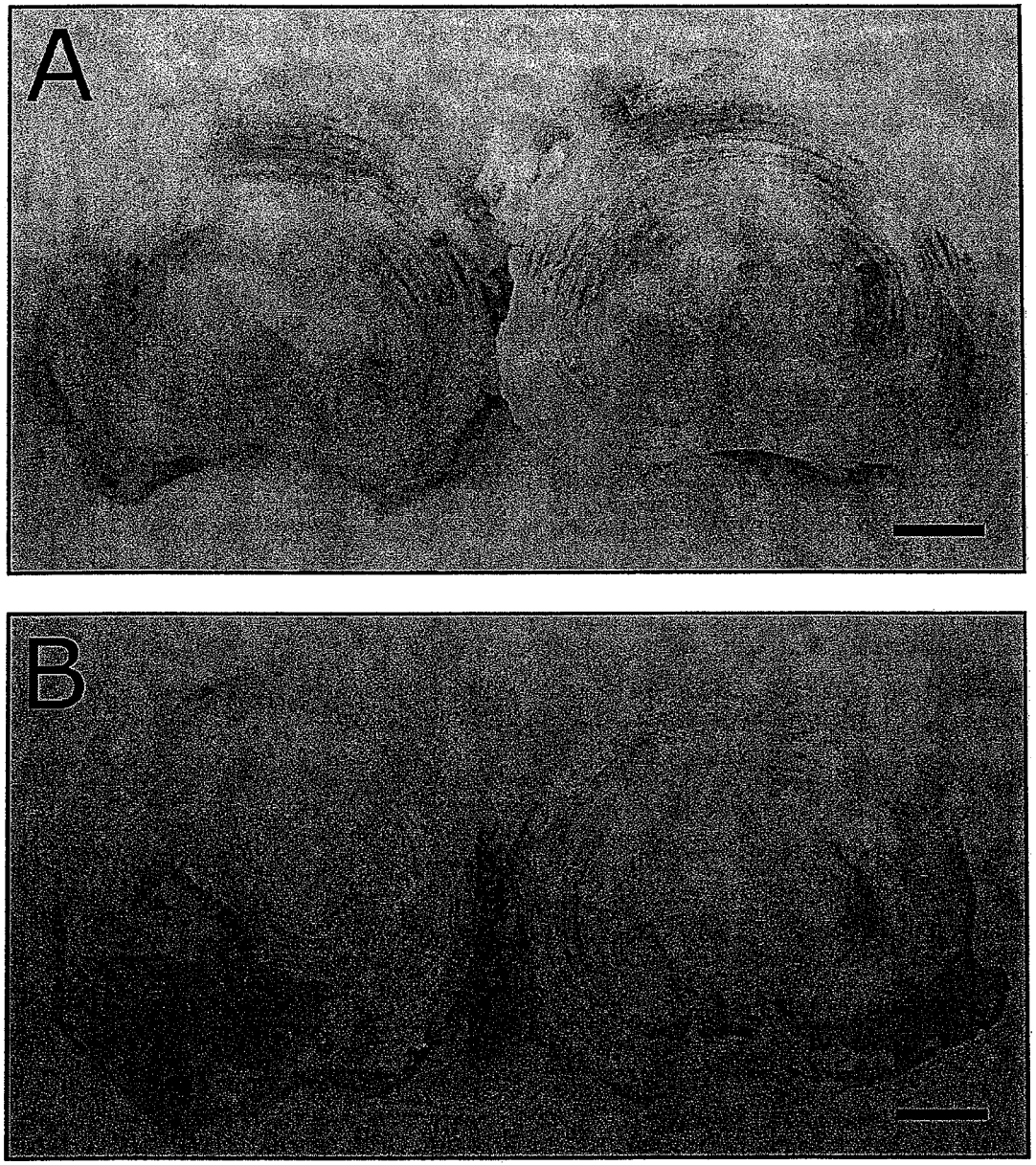
FIGS. 11A-B—Examples of genipin and BSA-TR diffusion in calf lumbar spinal discs after 1 hr at 37° C. 200 µl of 0.33% (w/v) GP (FIG. 11A) or 1 mg/ml BSA-TR (FIG. 11B) were injected into the disc of a single motion segment and incubated for 1 hr at 37° C. Discs were transected with scalpel, frozen at −20° C. overnight, and then thawed and photographed the following day. Bars=10 mm.

In order to observe the diffusion kinetics of these markers, GP (0.33% (w/v)) or BSA-TR (1 mg/ml) were dissolved in PBS and 200 µl injected at a depth of 1 cm into the discs of individual calf lumbar motion segments and incubated at 37° C. for 1, 3 or 6 hrs in sealed ZipLoc bags containing a sheet of paper towel moistened with $H_2O$. In initial experiments discs were injected at three sites, the dorsal and left and right lateral regions. In some cases, however, diffusion zones merged and were not possible to quantify and in subsequent experiments injections were limited to the left and right lateral regions. Following the incubations, each segment was transected with a scalpel and frozen overnight at −20° C. (to allow the color of the genipin to develop). The samples were then thawed, photographed and the area of each diffusion zone calculated using ImageJ software. Example photographs of both GP and BSA-TR diffusion zones after 1 hr are shown in FIG. 11.

Figure 12:
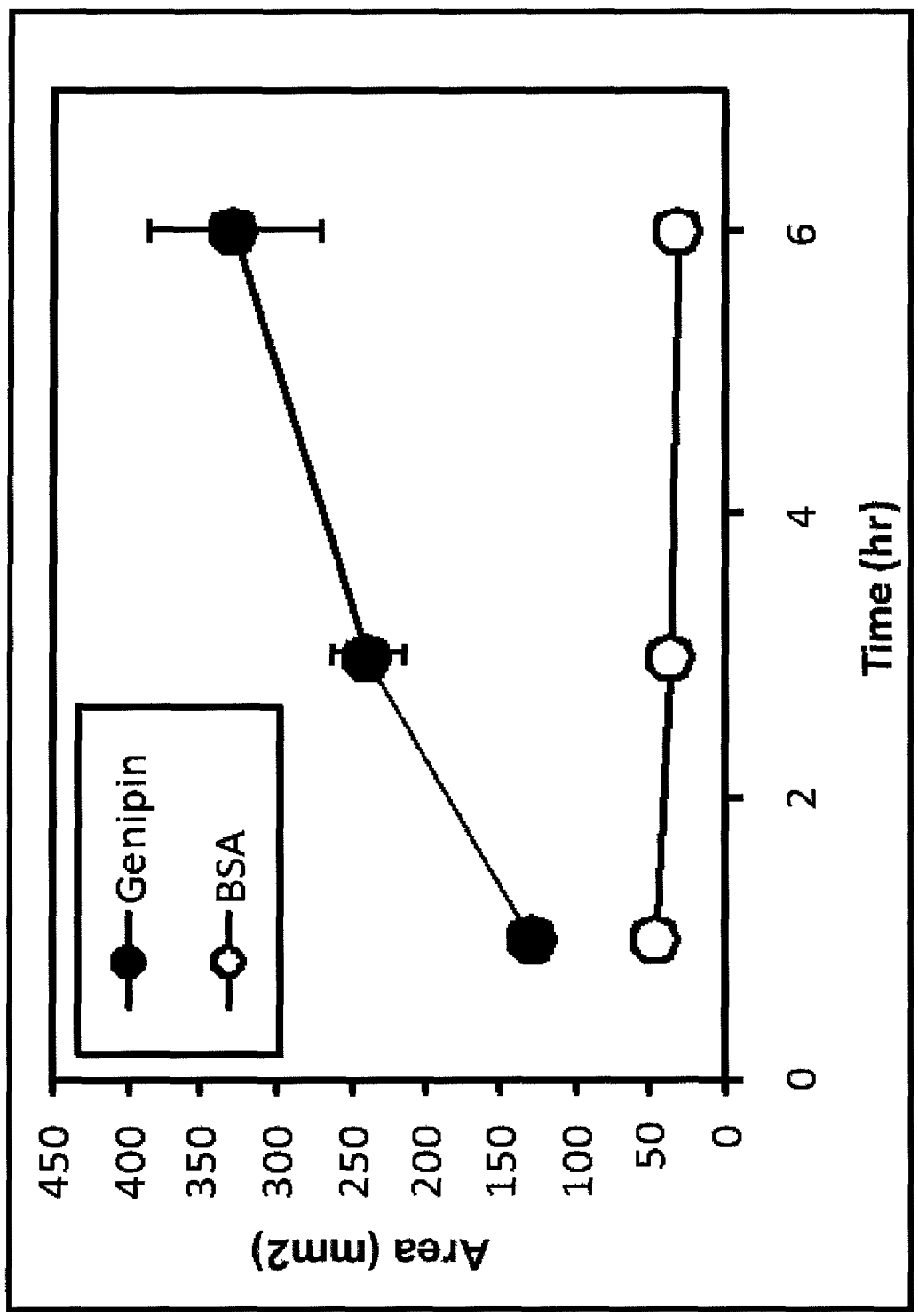
FIG. 12—Diffusion kinetics of genipin and BSA in calf lumbar spinal discs. 200 µl of 0.33% (w/v) or 1 mg/ml BSA-Texas Red were injected at a depth of 1 cm into the discs of individual calf lumbar motion segments and incubated for 1, 3 or 6 hours at 37° C. Samples were transected and the area of each diffusion zone at each time point and for each reagent was determined from photographs using ImageJ software.

GP demonstrated a clear time-dependant increase in the area of the diffusion zones (FIG. 12). In contrast BSA-TR did not appear to diffuse once injection. The areas of BSA-TR staining observed were presumably those generated by the hydrostatic pressure applied during injection. There appeared to be no significant diffusion of BSA-TR following injection into the disc, suggesting that the molecule was too large to be able to pass through the densely packed collagen fibrils of the annulus. There are two caveats to this observation. Firstly, prior testing has suggested a doubling of hydraulic permeability and associated increase in macromolecular transport with increased crosslinking of disc tissues. Secondly, these experiments did not simulate the diurnal pressure driven convective flow that would be seen in the in vivo situation. Consequently, although these experiments showed a lack of diffusion of the larger molecule, penetration could be greater in the in vivo situation with a large molecule crosslinking reagent.

Figure 13:
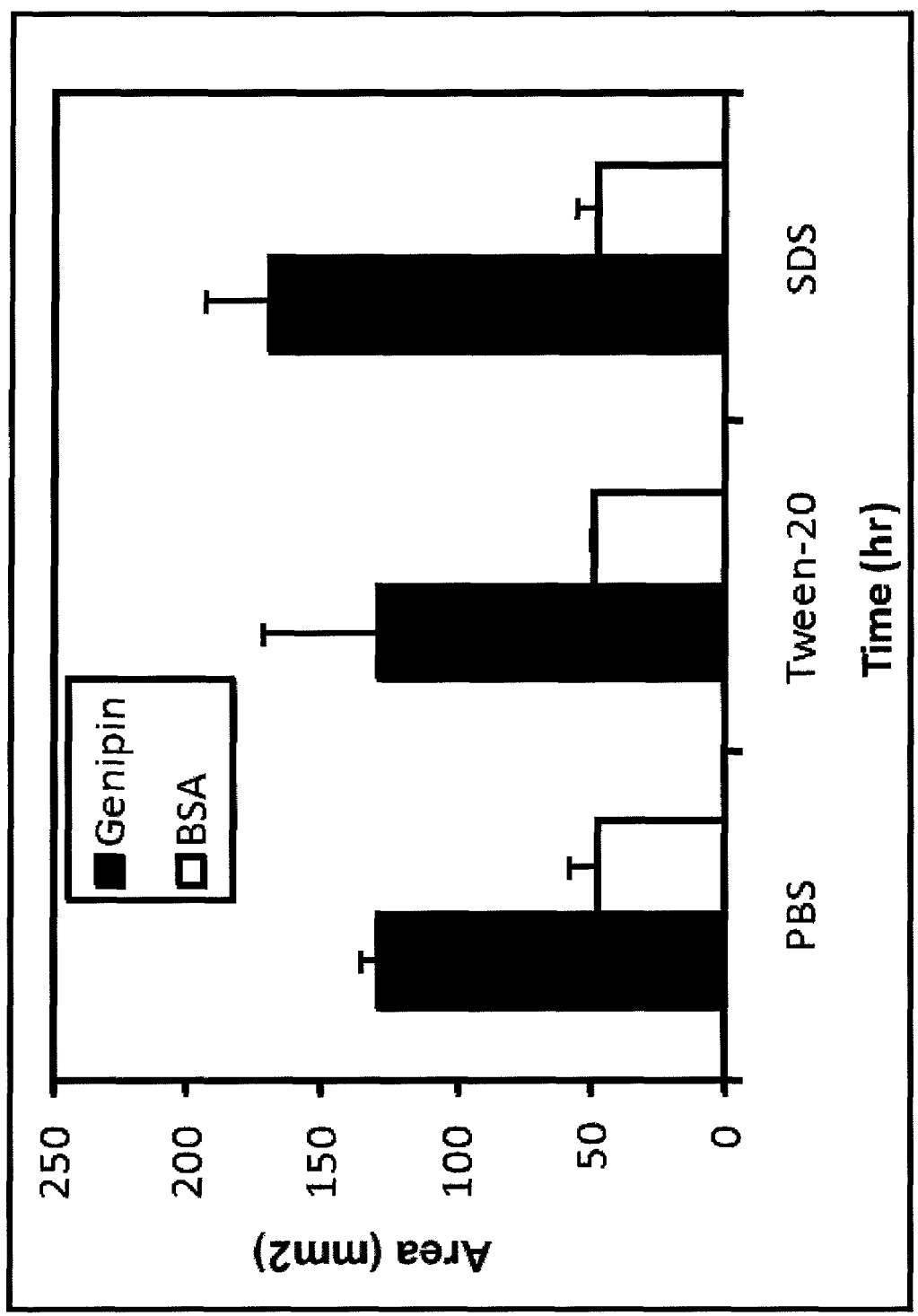
FIG. 13—Effect of surfactants on the diffusion of GP and BSA-TR. 200 µl of 0.33% (w/v) or 1 mg/ml BSA-Texas Red formulated in PBS in the absence of presence of 0.1% (w/v) of either Tween-20 or SDS were injected at a depth of 1 cm into the discs of individual calf lumbar motion segments. Segments were incubated for 1 hr at 37° C. and the samples were then transected and the area of each diffusion zone determined from photographs using ImageJ software.

In order to potentially maximize the diffusion of these reagents, the inventors next sought to determine whether this could be achieved through the addition of detergents. The inventors chose one mild, non-ionic surfactant (Tween-20) and one harsher anionic surfactant (SDS) for this purpose. Both 0.33% (w/v) GP and 1 mg/ml BSA-TR were formulated in either PBS alone or PBS containing 0.1% (w/v) of either SDS or Tween-20. These solutions were injected as described above and incubated at 37° C. for 1 hr. Neither surfactant appeared to have any effect on the mobility of BSA-TR through the tissue (FIG. 13). In contrast, SDS appeared to enhance the diffusion of GP through intervertebral disc tissue by approximately 30% under these conditions. A two-tailed t-test (assuming unequal variance) showed that this result was statistically significant (p=0.021). Tween-20, however, did not appear to enhance the diffusion of GP.

A summary of various optimizations is provided in Table 5. All of the diffusion experiments described above were conducted at least in triplicate and the results are tabulated in Table 6.

TABLE 5

Summary of optimization results for various crosslinking reagents

| Crosslinker | [Saturating] | pH | $T_{1/2}$ |
|---|---|---|---|
| EDC | 2.5-5 mM | 6 | <5 min |
| Genipin | 5-10 mM | 8-9 | 10-18 min |
| L-Threose | 50 mM | 8-9 | 2.5 hrs |
| D-Threose | 50 mM | nd* | nd |
| Methylglyoxal | 30-50 mM** | 8-9 | 14-20 min |
| Transglutaminase | >2 U/ml | 7-8 | tbd |
| Proanthrocyanidin | 0.1% | 5-9 | <5 min |
| Glutaraldehyde | 1-2 mM | 8-9 | <5 min |

*not determined
**at pH 7. At pH 8, [Saturating] was 5-10 mM.

TABLE 6

Summary of Diffusion Study Data

| | Time | | | | | | | | | |
|---|---|---|---|---|---|---|---|---|---|---|
| | 1 hr | | | 1 hr | | | 3 hr | | 6 hr | |
| Treatment | GP PBS | GP Tween | GP SDS | BSA PBS | BSA Tween | BSA SDS | GP | BSA | GP | BSA |
| | 127.7 A | 124.5 A | 187.1 A | 39.0 E | 46.7 D | 47.8 D | 228.6 G | 13.7 F | 329.0 H | 23.9 H |
| | 131.0 C | 174.7 B | 155.6 T | 42.1 N | 45.9 E | 56.1 E | 268.7 J | 35.6 G | 347.6 K | 32.3 L |
| | 110.7 H | 88.5 H | 200.2 T | 65.1 N | 50.7 O | 38.2 H | 216.5 J | 62.6 G | 252.5 K | 37.2 R |
| | 133.8 P | | 135.1 U | 43.5 N | | | 251.5 Q | | 392.9 M | |
| | 129.9 S | | 167.1 U | | | | | | | |
| | 133.0 S | | | | | | | | | |
| | 132.7 S | | | | | | | | | |
| Mean | 128.4 | 129.3 | 169.0 | 47.4 | 47.8 | 47.4 | 241.3 | 37.3 | 330.5 | 31.1 |
| SD | 8.1 | 43.3 | 25.6 | 11.9 | 2.5 | 9.0 | 23.3 | 24.5 | 58.5 | 6.8 |

Values are given as mm².
Each disc was injected at two or three locations.
The letters A-U represent individual motion segments from which the data were obtained.

Example 11

Use of Contrast Agents

During clinical application of NEXT, the crosslinking reagent is injected into the spinal disc. In order to ensure the accurate delivery of the crosslinker to the tissue, a biocompatible contrast agent is used and the procedure conducted fluoroscopically. The crosslinker is either formulated in the presence of a suitable contrast agent (e.g., iohexyl) or diluted with a commercially available and suitable contrast agent (e.g., Isovue 200). In the latter case, the crosslinker is formulated at a higher concentration to account for its dilution with the contrast agent and at a level to ensure that optimal concentration is maintained when the crosslinker contacts the target tissue.

\*\*\*

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VIII. List of References

The following references, to the extent that they provide exemplary procedural or other details supplementary to those set forth herein, are specifically incorporated herein by reference:

U.S. Pat. No. 3,436,407
Adams, *Spine,* 7:184-191, 1982.
Boyd-White and Williams, *Diabetes,* 45:348-353, 1996.
Buckwalter et al., *J. Bone Joint Surg.,* 75A: 1533-1548, 1993.
Buckwalter, *Spine,* 20:1307-14, 1995.
Chachra et al., *Biomaterials,* 17:1865-75, 1996.
Chellan and Nagaraj, *Arch. Biochem. Biophys.* 368:98-104, 1999.
Chen et al., In: *Age-related crosslinking alters tensile properties of articular cartilage,* 47th Annual Meeting, Orthop. Res. Soc., 128, 2001.
Chuang and Hedman, *Orthopaedic Trans.,* 32:1025, 2007.
Chung et al., *J. Biol. Chem.,* 245:6424-6435, 1970.
Deutman, *Acta Orthop. Scand.,* 63(5):571-575, 1992.
Duance et al., *Spine,* 23:2545-51, 1998.
Fu et al., *Diabetes,* 41(2):42-48, 1992.
Goel et al., *Spine,* 11(10):1008-1012, 1986.
Goel et., *Spine,* 20: 689-698, 1995.
Goel, *Spine,* 10(6):543-554, 1985.
Green, *European Spine J.,* 2: 209-214, 1993.
Greve et al., *Biochemica et Biophysica Acta,* 967:275-283, 1988.
Hedman et al., *Orthop. Res. Soc. Transactions,* 24:1017, 1999.
Hedman, In: *Use of non-destructive materials testing techniques to assess the degradation of intervertebral discs subjected to non-traumatic repetitive loads,* USC/GOS Annual Meeting, Calif., 2000.
Horner and Urban, *Spine,* 26:2543-9, 2001.
Kitano, *Clinical Orthopaedics and Related Res.,* 1993.
Kotilainen, *Acta Neurochir (Wien),* 120(3-4):143-149, 1993.
Kotilainen, *Ann. Chir. Gynaecol. Suppl.,* 209:1-50, 1994.
Kotilainen, *Duodecim.,* 114(11):1071-1073, 1998.
Laparra et al., *Plantes medicin. et Phytoth.,* 1977, 11, 133, 1977.

Masquelier et al., *J. Vit. Nutr. Res.*, 49:307-311, 1979.
Murata-Kamiya and Kamiya, *Nucleic Acids Res.*, 29:3433-3438, 2001.
Nakajima anb Ikada, *Bioconjug Chem.* 1995, 6(1), 123-130
Osti et al., *J. Bone Joint Surg Br.*, 74(5):678-682, 1992.
Panjabi et al., *J. Orthop. Res.*, 14(2):216-222, 1996.
Skotnicki, S; *Tetrahedron Lett.*, 35(2):197-200, 1994.
Sung et al., *Biomaterials*, 20(19): 1759-1772, 1999a.
Sung et al., *J. Biomed. Materials Res.*, 47:116-126, 1999b
Sung et al., *J. Biomed. Materials Res.*, 64:427-438, 2003.
Thompson et al. *Nature*, 414:773-776, 2001.
Urban et al., *Spine*, 29(23):2700-2709, 2004.
Wang et al., *Bone*, 23:67-72, 1998.
Watkins et al., *J. Biol. Chem.*, 262:7207-7212, 1987.
Zeeman et al., *J. Biomed. Materials Res.*, 46(3):424-433, 1999.
Zhang and Vogel, *J. Biol. Chem.*, 268(30):22420-22428, 1993.
Zhang et al., *J. Biol. Chem.* 279:20490-20500, 2004.

What is claimed:

1. A method of inducing genipin (GP)-mediated cross-linking in a native tissue having naturally-occurring collagen crosslinks within a living human body, comprising contacting said tissue with GP at about 20 mM or less and a combination of the following in a composition of about pH 8.0-9.5:
   (a) 50-500 mM phosphate ions; and
   (b) 50-250 mM 4-(2-hydroxyethyl)-1-piperazinepropane-sulfonic acid (EPPS) buffer.

2. The method of claim 1, wherein said GP is contacted at a concentration of 20 mM in 100 mM EPPS buffer at pH 9 with 100 mM phosphate ions.

3. The method of claim 1, wherein said tissue is located in a joint.

4. The method of claim 1, wherein said tissue is a spinal disc.

5. A composition of matter comprising about 5-20 mM genipin (GP) and about 50-250 mM EPPS at about pH 8.0-9.5 and 50-500 mM phosphate ions.

* * * * *